United States Patent
Redding

(10) Patent No.: US 10,252,244 B2
(45) Date of Patent: Apr. 9, 2019

(54) MESOPOROUS ACTIVATED CARBON

(71) Applicant: Evoqua Water Technologies LLC, Lowell, MA (US)

(72) Inventor: Adam M. Redding, State College, PA (US)

(73) Assignee: Evoqua Water Technologies LLC, Pittsburgh, PA (US)

( * ) Notice: Subject to any disclaimer, the term of this patent is extended or adjusted under 35 U.S.C. 154(b) by 0 days.

(21) Appl. No.: 15/895,635

(22) Filed: Feb. 13, 2018

(65) Prior Publication Data

US 2018/0178190 A1   Jun. 28, 2018

Related U.S. Application Data

(62) Division of application No. 14/775,781, filed as application No. PCT/US2014/026195 on Mar. 13, 2014, now Pat. No. 9,914,110.

(Continued)

(51) Int. Cl.
*B01J 20/20* (2006.01)
*B01J 20/32* (2006.01)
(Continued)

(52) U.S. Cl.
CPC ......... *B01J 20/20* (2013.01); *B01J 20/28011* (2013.01); *B01J 20/28083* (2013.01); *B01J 20/3078* (2013.01); *B01J 20/3204* (2013.01); *B01J 20/3236* (2013.01); *B01J 20/3416* (2013.01); *B01J 20/3475* (2013.01); *C01B 32/30* (2017.08); *C01B 32/306* (2017.08); *C01B 32/348* (2017.08); *C01B 32/354* (2017.08); *G01N 15/088* (2013.01);
(Continued)

(58) Field of Classification Search
CPC .... B01J 20/20; B01J 20/3078; B01J 20/3475; B01J 20/28083; B01J 20/3204; B01J 20/3416; B01J 20/3236; B01J 20/28011; B01J 2220/4881; B01J 2220/485; G01N 15/088; G01N 2015/0866; C01B 31/125; C01B 31/08; C01B 31/085; C01B 31/083; C02F 1/283; C02F 2101/36; C01P 2006/16
See application file for complete search history.

(56) References Cited

U.S. PATENT DOCUMENTS 4,576,929 A   3/1986   Shimazaki
5,013,698 A   5/1991   Lonsinger et al.
(Continued)

FOREIGN PATENT DOCUMENTS

JP   H8-119614      5/1996
JP   2001-048515 A  2/2001

OTHER PUBLICATIONS

Okada, Kiyoshi, et al. "Water vapor adsorption of CaCl2-impregnated activated carbon." Materials Research Bulletin 45.11 (2010): 1549-1553.*

(Continued)

*Primary Examiner* — Richard M Rump

(57) ABSTRACT

Mesoporous activated carbon having a mesopore structure of at least about 10%. In at least some embodiments, the activated carbon may be coconut shell-based. The enhanced activated carbon may have an intraparticle diffusion constant of at least about 40 $mg/g/hr^{1/2}$.

12 Claims, 21 Drawing Sheets

Related U.S. Application Data

(60) Provisional application No. 61/793,438, filed on Mar. 15, 2013.

(51) Int. Cl.

| | | |
|---|---|---|
| *B01J 20/34* | (2006.01) | |
| *B01J 20/28* | (2006.01) | |
| *B01J 20/30* | (2006.01) | |
| *G01N 15/08* | (2006.01) | |
| *C01B 32/30* | (2017.01) | |
| *C01B 32/354* | (2017.01) | |
| *C01B 32/306* | (2017.01) | |
| *C01B 32/348* | (2017.01) | |
| *C02F 1/28* | (2006.01) | |
| *C02F 101/36* | (2006.01) | |

(52) U.S. Cl.
CPC .. *B01J 2220/485* (2013.01); *B01J 2220/4881* (2013.01); *C01P 2006/16* (2013.01); *C02F 1/283* (2013.01); *C02F 2101/36* (2013.01); *G01N 2015/0866* (2013.01)

(56) References Cited

U.S. PATENT DOCUMENTS

| | | |
|---|---|---|
| 5,238,470 A | 8/1993 | Tolles et al. |
| 5,292,708 A | 3/1994 | Karl |
| 5,368,754 A | 11/1994 | Von Klock et al. |
| 5,482,915 A | 1/1996 | Golden et al. |
| 5,714,126 A | 2/1998 | Frund |
| 5,726,118 A | 3/1998 | Ivey et al. |
| 5,860,391 A | 1/1999 | Maxwell et al. |
| 5,948,398 A | 9/1999 | Hanamoto et al. |
| 6,057,262 A | 5/2000 | Derbyshire et al. |
| 6,120,698 A | 9/2000 | Rounds et al. |
| 6,248,691 B1 | 6/2001 | Gadkaree et al. |
| 7,588,687 B2 | 9/2009 | Davankov et al. |
| 2005/0150835 A1 | 7/2005 | Vo |
| 2005/0173297 A1 | 8/2005 | Toida |
| 2006/0240979 A1 | 10/2006 | Hirahara et al. |
| 2008/0207442 A1 | 8/2008 | Pfeifer et al. |
| 2012/0085708 A1 | 4/2012 | Redding |
| 2012/0174936 A1 | 7/2012 | Branton et al. |
| 2015/0376015 A1 | 12/2015 | Yanagi et al. |

OTHER PUBLICATIONS

Cannon, Fred S., et al. "Reaction mechanism of calcium-catalyzed thermal regeneration of spent granular activated carbon." Carbon 32.7 (1994): 1285-1301.*
Rajaković, Lj V., and M. Dj Ristić. "Sorption of boric acid and borax by activated carbon impregnated with various compounds." Carbon 34.6 (1996): 769-774.*
Ryu, J., and Y. Kato. "Water Sorption of CaCl~ 2 Added Porous Materials as Heat Storage Media." Bulletin-Research Laboratory for Nuclear Reactors 29.1/2 (2005): 97.*
Knappe, Detlef RU, et al. "Effect of calcium on thermal regeneration of GAC." Journal (American Water Works Association) (1992): 73-80.*
Henning et al., "Carbon, 5. Activated Carbon," pp. 1-27, Wiley-VCH Verlag GmbH & Co., 2010.
Capon, et al, "Compensation Effect in the Acfivtion of Fibrous Chars Prepared from Viscose," Carbon vol. 21 No. 1, pp. 75-80, 1983, Pergamon Press.
Wigmans, "Fundamentals and Practical Implications of Activated Carbon Production by Partial Gasification of Carbonacelous Materials," Proceedings of the NATO Advanced Study Institute on Carbon and Coal Gasification—Science and Technology, pp. 559-560, 1986.
Itodo, et al, "Application of Methylene Blue and Iodine Adsorption in the Measurement of Specific Surfasce Area by Four Acid and Salt Treated Activated Carbons," New York Science Journal, 2010;3 (5), pp. 25-33, www.sciencepub.net/newyork/ny0305/05_2343_surface_ny0305_25_33.pdf.
Japanese Industrial Standards JIS K 1474, "Listing and Description of Characterization Techniques for Activated Carbons," Section 6.1.1.2 Methylene Blue Adsorption Performance, p. 9.
Greenwald, et al, "A Rapid Kinetic Dye Test to Predict the Adsorption of 2-Methyliobomeol Onto Granular Activated Carbon and to Identify the Influence of Pore Volume Distributions," Water Research 68, pp. 784-792, 2015.
Redding, et al., "A Novel Kinetic Dye Test for Prediction of Activated Carbon Performance," American Water Works Association, AWWA WQTC Conference Proceedings, pp. 1-53, 2013.
Redding, "Xylenol Orange Dye Test Method," pp. 1-6, 2014, https//www.astm.org/WorkItems/WK47401.htm.
Alau, KK et al. Removal of Dyes from Aqueous Solution Using Neem (*Azadirachta indica*) Husk as Activated Carbon. Archives of Applied Science Research. 2010. vol. 2 (5). pp. 456-461; abstract; pp. 457, 459-460.
Aroua, MK et al. Real-time determination of kinetics of adsorption of lead(II) onto palm shell-based activated carbon using ion selective electrode. Bioresource Technology. 2008. vol. 99 pp. 5786-5792; abstract; figure 2; p. 579.
Boparai, HK et al. Kinetics and thermodynamics of cadmium ion removal by adsorption onto nano zero valent iom particles. Journal of Hazardous Materials. 2010; entire document.
Cannon, Fred S. et al., "Reaction Mechanism of Calcium-Catalyzed Thermal Regeneration of Spent Granular Activated Carbon", Carbon vol. 32, No. 7 (1994), pp. 1285-1301.
Cazorla-Amoros, D. et al., "Selective Porosity Development by Calcium-Catalyzed Carbon Gasification", Carbon, vol. 34, No. 7 (1996) pp. 869-878.
Hu et al., "Preparation of High-Surface-Area Activated Carbons from Coconut Shell" in Microporous and Mesoporous Materials vol. 27 pp. 11-19 1999.
International Search Report and Written Opinion from corresponding PCT Application Serial No. PCT/US2014/026195 dated Jul. 8, 2014.
Knappe, Detlef, R. U. et al., "Effect of Calcium on Thermal Regeneration of GAC", American Water Works Association, (Aug. 1992), pp. 73-80.
Lastoskie, Christian, et al., "Pore Size Distribution Analysis of Microporous Carbons: A Density Functional Theory Approach", Journal of Physical Chemistry, 97 (1993) pp. 4786-4796.
Leboda, R. et al., "Effect of Calcium Catalyst Loading Procedure on the Porous Structure of Active Carbon from Plum Stories Modified in the Steam Gasification Process", Carbon vol. 36, No. 4, (1998) pp. 417-425.
Marsh, Harry, "The Effects of Impregnation of Coal by Alkali Salts upon Carbonization Properties", Fuel Processing Technology 2 (1979) pp. 61-75.
Otto, K. et al., "Catalytic Steam Gasification of Graphite: Effects of Calcium, Strontium, and Barium With and Without Sulfur", Carbon 17 (1979) pp. 351-357.
Radovic, Ljubisa, R. et al., "Combined Effects of Inorganic Constituents and Pyrolysis Conditions on the Gasification Reactivity of Coal Chars", Fuel Processing Technology, 10 (1985) pp. 311-326.
Ravikovitch, Peter I. et al., "Unified Approach to Pore Size Characterization of Microporous Carbonaceous Materials from N2, Ar and CO2 Adsorption Isotherms", Langmuir, 16, (2000) pp. 2311-2320.

* cited by examiner

MESOPOROUS ACTIVATED CARBON

FIELD

One or more aspects relate generally to activated carbon. More particularly, one or more aspects relate to mesoporous activated carbon, as well as the production, characterization, and testing thereof.

BACKGROUND

Activated carbon is widely used in gas purification, water purification, metal extraction, and waste water treatment among other applications. Activated carbon is generally a form of carbon that has been physically or chemically processed to increase its porosity and surface area available for adsorption and chemical reactions. Powdered activated carbon (PAC) and granular activated carbon (GAC) are among common forms.

SUMMARY

Aspects relate generally to activated carbon and various techniques for the production, characterization, and testing of mesoporous activated carbon.

In accordance with one or more embodiments, a coconut shell-based activated carbon may have an intraparticle diffusion constant of at least about 40 mg/g/hr$^{1/2}$. In some embodiments, the coconut shell-based activated carbon may have an intraparticle diffusion constant of at least about 100 mg/g/hr$^{1/2}$. In some embodiments, the coconut shell-based activated carbon may have an apparent density of about 0.43 g/cc to about 0.49 g/cc. In other embodiments, the coconut shell-based activated carbon may have an iodine number of about 1000 mg/g or greater. In some embodiments, the coconut shell-based activated carbon may be associated with a contact pH level of about 9 to about 10. In some embodiments, the coconut shell-based activated carbon is reactivated carbon.

In accordance with one or more embodiments, a method of producing an enhanced activated carbon may comprise providing a predominantly microporous virgin activated carbon, introducing an aqueous calcium-based catalyst to the virgin activated carbon to produce a catalyst impregnated activated carbon, heating the catalyst impregnated activated carbon at a pyrolysis temperature until a mesopore volume of at least about 10% is achieved while substantially maintaining a micropore structure associated with the virgin activated carbon to produce the enhanced activated carbon, subjecting the enhanced activated carbon to a dye test to determine its intraparticle diffusion constant, and screening the enhanced activated carbon based on a threshold dye test number.

In some embodiments, the threshold dye test number may be at least about 40 mg/g/hr$^{1/2}$ for xylenol orange dye. In some embodiments, the method may be associated with a mass loss of at least about 10%. The aqueous calcium-based catalyst may comprise calcium chloride. The aqueous calcium-based catalyst may comprise a chelator. In some embodiments, the chelator may comprise citric acid. In at least some embodiments, the virgin activated carbon is coconut shell-based. In some embodiments, the virgin activated carbon is at least about 90% microporous. The catalyst impregnated activated carbon may be maintained at an intermediate temperature prior to reaching the pyrolysis temperature. The virgin activated carbon may be sprayed with or soaked in the aqueous calcium-based catalyst. In some embodiments, the method may further comprise oxidizing the catalyst impregnated activated carbon with carbon dioxide. In other embodiments, the catalyst impregnated activated carbon may be oxidized with carbon dioxide and steam.

In accordance with one or more embodiments, a method for predicting the performance of an activated carbon may comprise providing an activated carbon source, subjecting a sample representative of the activated carbon source to a dye test, determining a dye test number of the sample, and correlating the dye test number to an expected performance to predict the performance of the activated carbon source. In some embodiments the activated carbon source may comprise reactivated carbon.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures. The figures are provided for the purposes of illustration and explanation and are not intended as a definition of the limits of the invention. In the figures.

DETAILED DESCRIPTION

Figure 1:
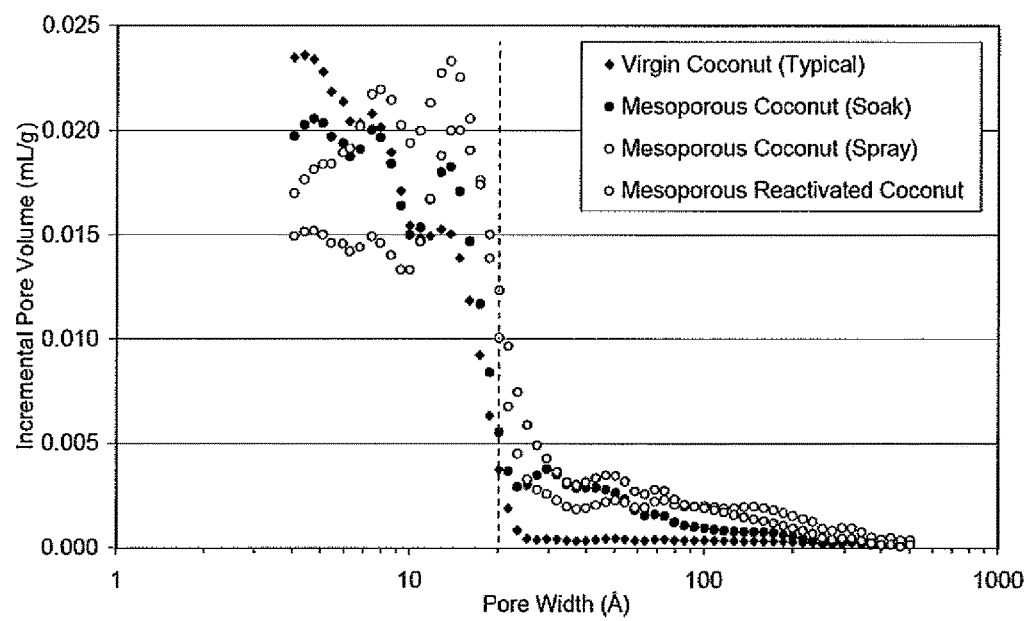
FIGS. 1-21 present data referenced in the detailed description and accompanying examples.

In accordance with one or more embodiments, an activated carbon may be treated to increase its mesopore volume while retaining its inherent micropore structure. The enhanced mesopore structure may provide improved adsorption kinetics and adsorption capacity for larger molecular weight compounds. The intact micropore structure may provide volatile organic compounds (VOC) adsorption capacity. The modified pore structure of the activated carbon material may lead to longer bed life between carbon exchanges, and lower life cycle costs. The enhanced activated carbon may conform to various industry defined physical and performance requirements for various applications, such as leachability for potable water production. The enhanced activated carbon may provide trace VOC removal capacity and adsorptive performance to remove taste, odor, and other organic contaminants. The enhanced activated carbon may be subsequently reactivated.

In accordance with one or more embodiments, enhanced activated carbon produced according to the techniques described herein may also beneficially be characterized, screened for specific properties, and tested for optimization, for example, based on predicted performance.

In accordance with one or more embodiments, the activated carbon may be powdered activated carbon (PAC) or granular activated carbon (GAC). An activated carbon material which is predominantly microporous in structure may be chemically treated and/or thermally modified to increase its mesopore volume. In at least some embodiments, any starting material that has a micropore volume of at least about 90% may be treated to increase its mesopore volume. Such treatment may result in no significant loss of micropore structure although the relative percentage of micropore volume with respect to total pore volume may be altered. As a result, during adsorption the transport rate of organic contaminants into the micropores may be increased and/or less hindered by competing adsorbates such as natural organic matter. In some non-limiting embodiments, a starting material may be more than about 95% microporous in volume. In some non-limiting embodiments, a starting material may be less than about 5% mesoporous. In other embodiments, a starting material may be less than about 10% mesoporous. In still other embodiments, a starting material may be less than about 20% mesoporous. In at least some embodiments, the starting material may have an intraparticle diffusion constant or "xylenol orange dye number" of less than 40 $mg/g/hr^{1/2}$ as discussed herein.

The mesopore volume of an activated carbon treated in accordance with one or more non-limiting embodiments may be increased. In some embodiments, enhanced activated carbon may have a mesopore volume of up to about 10%. Thus, in some non-limiting embodiments, mesopore volume may be increased from less than about 5% to up to about 10%. In other embodiments, enhanced activated carbon may have a mesopore volume of up to about 20%. In at least some embodiments, treated activated may have a mesopore volume of up to about 30%. For purposes of one or more disclosed embodiments, the term micropore refers to a pore of about 2 to about 20 Angstroms in diameter while the term mesopore refers to a pore of about 20 to about 500 Angstroms in diameter based on definitions commonly known to those skilled in the art and as adopted by the International Union of Pure and Applied Chemistry (IUPAC). Percentages relating to micropore volume and mesopore volume, or percentages in conjunction with the terms microporous and mesoporous, used above and throughout may generally refer to percentage of total pore volume as calculated from gas adsorption isotherms and as commonly recognized by those skilled in the art.

The mesopore volume of an activated carbon treated in accordance with one or more non-limiting embodiments may be increased as reflected by an increased intraparticle diffusion constant or dye test number. In some non-limiting embodiments, an enhanced activated carbon may have a xylenol orange dye number of at least 40 $mg/g/hr^{1/2}$. In some embodiments, enhanced activated carbon may have a xylenol orange dye number of at least 100 $mg/g/hr^{1/2}$. In some specific non-limiting embodiments, enhanced activated carbon may have a xylenol orange dye number of at least 140 $mg/g/hr^{1/2}$. For purposes of one or more disclosed embodiments, the term xylenol orange number refers to a value obtained through dye testing in accordance with protocols described herein.

Any predominantly microporous activated carbon may be treated to enhance its performance. In some embodiments, a starting material to be enhanced may be virgin activated carbon. In other embodiments, a starting material may be spent activated carbon which has been used for treatment and may have reached its adsorption capacity. In some non-limiting embodiments, spent activated carbon used as a starting material may have a calcium content of greater than or equal to about 0.5% by weight. In other non-limiting embodiments, spent activated carbon used as a starting material may have a calcium content of greater than or equal to about 1% by weight. In at least one embodiment, the starting material may have already undergone at least one physical or chemical treatment process, for example, as in the case of a virgin activated carbon. In other embodiments, the starting material may not have undergone previous treatment. In accordance with one or more embodiments, an enhanced activated carbon such as a mesoporous activated carbon may be produced from various carbonaceous source materials including nutshells, peat, wood, coir, lignite, coal, and petroleum pitch. In some embodiments, the starting material may be coconut-shell based. In some non-limiting embodiments, an enhanced activated carbon may be a coconut shell-based activated carbon. In at least one embodiment, Westates® coconut shell-based granular activated carbon (AquaCarb® 830C, 1230C and 1230AWC) commercially available from Siemens Industry, Inc. (Warrendale, Pa.) may be treated and enhanced. In some embodiments, the starting material may be less than about 10% mesoporous. In at least some embodiments, the starting material may be less than about 5% mesoporous. In some embodiments, the starting material may have at most about 1% to about 5% mesoporous volume and about 95% to about 99% microporous volume. In at least some non-limiting embodiments, the starting material may be about 95% microporous and about 5% mesoporous.

In accordance with one or more embodiments, an enhanced activated carbon may have a mesopore volume of about 5% to about 50% with the balance being substantially microporous. In at least some embodiments, the mesopore volume may be about 10% to about 30% with the balance being substantially microporous. In still other embodiments, the mesopore volume may be about 15% to about 25% with the balance being substantially microporous. There may be macropores or other pore structures, such as those having a diameter of greater than about 500 Angstroms, in addition to the mesopores and micropores but they are not believed to measurably influence performance of the activated carbon. In some embodiments, enhanced coconut shell-based activated carbons may offer the benefits of traditional coconut shell-based activated carbons, as well as the benefits of bituminous coal based carbons. In at least one or more embodiments, any lignocellulosic material may be used as a natural source of microporous activated carbon starting material.

In accordance with one or more embodiments, the rate of activation of a starting material may be increased. In some non-limiting embodiments, an activated carbon starting material may be oxidized and/or gasified to increase its porosity. In at least one embodiment, treatment of an activated carbon starting material may be catalyzed. Thermal activation may be catalyzed to increase the rate of activation. Various catalysts may be used to catalyze the rate of activation. In some embodiments, a metal catalyst may be used. In at least some embodiments, a transition metal catalyst may be used. In one non-limiting embodiment, the rate of activation may be calcium-catalyzed. Various sources of calcium, such as calcium chloride, calcium acetate and calcium propionate may be used. In accordance with one or more embodiments, a catalyst may be present in solution for application to a starting material. Any solvent may be used. In some preferred embodiments, an aqueous solvent may be used.

In some non-limiting embodiments, a catalyst may already be present in a material to be treated, such as in spent activated carbon which may be treated for reactivation purposes. The catalyst may be present due to previous activation or due to prior use in the treatment of a process stream. Carbon reactivation may offer environmental benefits, minimizing waste by recycling and reusing spent carbon. Thermal or chemical reactivation may restore the surface area and pore volume of spent carbon to a point close to that of a virgin carbon. The process of carbon reactivation may be very similar to the process of treating virgin activated carbon. Reactivated carbons in accordance with one or more embodiments may provide a cost-effective alternative to virgin carbon while providing excellent performance in various treatment applications. In some embodiments, a spent activated carbon which has or previously had a desired mesopore volume may be reactivated. In other embodiments, a spent activated carbon that was not previously enhanced to exhibit a desired mesopore volume may be reactivated to produce an enhanced activated carbon having the desired mesopore volume.

In accordance with one or more embodiments, a chelator may be implemented. In some embodiments, a catalyst may be introduced using a chelator. In at least one embodiment, the catalyst source, such as calcium chloride for example, may be impregnated with a chelator. In general, any soluble chelator may be used. In at least one non-limiting embodiment, citric acid may be used as a chelator. In other non-limiting embodiments, EDTA or another known chelator may be used. In at least some non-limiting embodiments, no chelator is used.

In accordance with one or more embodiments, a catalyst may aid oxidant transfer to a surface of the activated carbon. Carbon monoxide may be produced by uncatalyzed gasification of oxidation by steam. A metal catalyst precursor may convert to an active oxide, such as a metal oxide or a transition metal oxide, via reaction with carbon dioxide and/or steam. Carbon dioxide may be generated from steam and carbon monoxide via the gas phase water-gas shift reaction. The oxidant may diffuse to the interior of the activated carbon grain and chemisorb to metal oxide crystallites. The oxidant may diffuse to the metal oxide-carbon interface and to a free active carbon site. Solid carbon-oxygen functional groups may gasify to form carbon monoxide. The gasification process may be associated with mass loss via void formation that may result in increased mesopore volume. The dispersion of the oxide may control the resulting crystallite size. For example, if the calcium is not dispersed well in the activated carbon, the oxidation may take place at only a few sites resulting in an overly focused burn-off. When well dispersed, the result of the oxidation is also well dispersed and many relatively small mesopores are created rather than a few relatively larger mesopores. Oxidant transfer may occur most rapidly at the crystallite sites and is therefore not available to more slowly oxidize non-catalytic areas or surfaces. Without the catalyst, burn-off may be relatively slow and result only in new micropore volume.

In accordance with one or more embodiments, an aqueous catalyst solution may be applied to a starting material. In some embodiments, the starting material may be soaked in the aqueous catalyst solution. In other embodiments, the starting material may be sprayed with the aqueous catalyst solution. Concentration of the aqueous catalyst solution may be adjusted based on the application method. For example, in some non-limiting embodiments, starting material may be sprayed with a catalyst solution having a chelator concentration of about 5% to about 30% or greater by weight. In some non-limiting embodiments, the chelator concentration of a sprayed catalyst solution may be about 15%. In other non-limiting embodiments, starting material may be soaked in a catalyst solution having a chelator concentration of about 3% to about 15% by weight. In some non-limiting embodiments, the chelator concentration of a catalyst solution in which starting material is soaked may be about 7%. In some embodiments, the chelator may facilitate distribution of the catalyst.

In accordance with one or more embodiments, the starting material may have undergone a physical or chemical pre-treatment prior to catalysis. In other embodiments, no pre-treatment may have occurred. The aqueous catalyst solution may include a source of a catalyst, such as calcium chloride. A chelator, such as citric acid, may also be present. The catalyst may be impregnated with the chelator. The starting material may be sprayed with or soaked in the aqueous catalyst solution for a predetermined period of time. In some embodiments involving soaking, the starting material may be soaked in the catalyst solution for about 1 hour to about 24 hours. In some non-limiting embodiments, the starting material may be soaked for about 12 hours. The liquid may then be removed, such as by vacuum filtration.

The catalyzed material may then be heated up to a pyrolysis temperature. The pyrolysis temperature may depend on the material to be treated. In some embodiments, the pyrolysis temperature may be at least about 600° C. In some embodiments, a pyrolysis temperature of about 600° C. to about 1200° C. may be used. In some specific non limiting embodiments, a pyrolysis temperature of about 800° C. to about 1100° C. may be used. In at least some non-limiting embodiments, a temperature of about 900° C. to about 1000° C. may be used. The heating may be staged such that one or more intermediate temperatures is achieved prior to reaching the pyrolysis temperature. An intermediate temperature may be maintained for a predetermined period of time prior to further heating. Parameters and conditions associated with one or more intermediate temperatures may vary. In some embodiments, the catalyzed material may be heated in steam, carbon dioxide, nitrogen, or mixtures of the gases during a first heating stage. The catalyzed material may then be heated in nitrogen, carbon dioxide and/or steam during a second heating stage. In other embodiments, a single heating stage involving steam, carbon dioxide and/or nitrogen may be implemented. In some specific non-limiting embodiments, carbon dioxide may be used as a sole oxidant. In other specific non-limiting embodiments, carbon dioxide in conjunction with steam may be used as oxidant.

Heating at the pyrolysis temperature may continue until a desired mass loss is achieved, such as about 5% to about 30%. A degree of mass loss may depend on a desired ratio of micropore and mesopore volume as further mass loss in the presence of the catalyst will produce additional mesopore volume thus reducing the total fraction of micropore volume. Thus, during enhancement, the percentage of mesopore volume may increase and the percentage of micropore volume may decrease as a function of total pore volume while still preserving the micropore structure and enhancing the mesopore structure of the carbon material. In some non-limiting embodiments, mass loss of about 10%, 20%, 30%, 40% or 50% may be achieved. Upon achieving a pyrolysis temperature, mass loss may be a function of treatment time and oxidant addition, for example, the mass of steam and/or carbon dioxide per mass of activated carbon per time. In some specific non-limiting embodiments, a residence time of about two hours in a kiln with 1 pound of steam per pound of GAC per hour may be used. To maintain integrity of the particles, mass loss may be generally limited to about 20% in some embodiments. In at least one non-limiting preferred embodiment, mass loss of about 10% may be achieved. The resulting treated activated carbon may then be cooled, preferably rapidly, with steam and/or nitrogen flow. In some non-limiting preferred embodiments, steam may be used for cooling.

In accordance with one or more embodiments, the metal catalyst may serve to increase the rate of carbon gasification by increasing oxidant transfer to the activated carbon surface. The catalyst does not act in a traditional manner in that it does not lower the activation energy required for gasification. At activation temperatures the organic chelator is oxidized and gasifies from the carbon surface as an organic contaminant does typically at reactivation temperatures. The chelator facilitates achieving a sufficient concentration and homogeneous distribution of metal catalyst within the activated carbon, such that the catalyst is at a level to sufficiently aid gasification. The catalyst may remain in the enhanced activated carbon product and future reactivation of the material may be adjusted to limit any excessive gasification of the material.

In accordance with one or more embodiments, a mesoporous activated carbon material may be associated with a specified mesh size. Some non-limiting mesh size examples for the mesoporous activated carbon product include 8 by 30, 12 by 30 and 12 by 40. An effective size of the mesoporous activated carbon product may also vary. Some non-limiting examples are about 0.8 mm to about 1.1 mm, about 0.6 mm to about 0.85 mm or about 0.55 mm to about 0.75 mm.

In accordance with one or more embodiments, a mesoporous activated carbon material may be associated with a specific iodone number. The iodine number may be used to predict performance across multiple carbon types (for example, bituminous, coconut, lignite, etc.). The iodine number may indicate an amount of micropores and may be used as a measure of the activated carbon's capacity. The standards for measuring iodine number are given in ASTM D4607. Some non-limiting examples of enhanced activated carbons may have an iodine number of about 500 mg of iodine per gram of carbon or greater. Some non-limiting examples of enhanced activated carbons may have an iodine number of about 1000 mg iodine/g carbon or greater. Some non-limiting examples of enhanced activated carbons may have an iodine number of about 1000 to about 1400 mg/g.

In accordance with one or more embodiments, some non-limiting examples of enhanced activated carbons may be characterized by an apparent density of about 0.43 g/cc to about 0.49 g/cc. Some non-limiting examples of enhanced activated carbons may be characterized by a hardness of about 95. Some non-limiting examples of enhanced activated carbons may be characterized by an abrasion rating of about 85. Some non-limiting examples of enhanced activated carbons may be associated with a contact pH level of about 9 to about 10.

In accordance with one or more embodiments, mesoporous activated carbon may be used for organic contaminant removal. In some embodiments, the mesoporous activated carbon may be implemented in any aqueous-phase application. Mesoporous activated carbon may be implemented in a fluidized bed associated with a liquid or vapor phase carbon treatment system. Disinfection byproducts and precursors thereof, as well as tastes and odors, may be removed from surface water. High performance VOC removal in groundwater sources may also be accomplished. Bulk organic and total organic carbon removal may also be facilitated.

In at least certain embodiments, the mesoporous activated carbon may be used in those applications where contact time is limited or a high background total organic carbon (TOC) concentration exists. In some nonlimiting embodiments, halogenated organics such as trihalomethanes may be removed. In at least one nonlimiting embodiment, chloroform may be removed. Tastes and odors, pesticides, polycyclic aromatic hydrocarbons, polychlorinated biphenyls, endocrine disruptors, pharmaceuticals and personal care products may all be treated with mesoporous activated carbon in accordance with one or more non-limiting embodiments.

In accordance with one or more non-limiting embodiments, wastewater may be contacted with enhanced activated carbon in GAC form in a semi-batch or continuous process. In some non-limiting embodiments, fixed bed, expanded bed, moving bed or fluidized bed adsorption processes may be used in conjunction with the enhanced activated carbons discussed herein. Various factors may impact contactor design including particle size, column diameter, flow rate of incoming wastewater, residence time, adsorption bed height, pressure drop and breakthrough time. In general, as the wastewater moves through the enhanced activated carbon, pollutants may be adsorbed via movement from the wastewater to the carbon bed. The overall adsorption process may be dominated by a mass transfer step from the wastewater bulk to the surface of the carbon particle through the boundary layer surrounding the particle. Internal diffusion through the carbon pores and adsorption onto the surface of the particle may also be involved. In other non-limiting embodiments, enhanced activated carbon in PAC form may be introduced in bulk to a solution for treatment. PAC may generally be associated with a smaller particle size and may be added directly to other process units such as raw water intakes, rapid mix basins, clarifiers and gravity filters rather than being used in a dedicated adsorber vessel.

In accordance with one or more embodiments, enhanced activated carbon may be identified, characterized, screened and/or tested subsequent to production. In at least some embodiments, enhanced activated carbon having one or more desired properties may be selected for and separated from standard activated carbon. In some non-limiting embodiments, performance of activated carbon such as enhanced activated carbon may be predicted.

One method for identifying enhanced carbon is by using gas porosimetry. This method is not widely available, expensive (about $900/sample), and time consuming (about 3 to 4 days/sample). Other standardized carbon test methods such as Iodine Number, Methylene Blue Number, Molasses Number, may not be capable of differentiating the enhanced carbon products or may do so inefficiently.

In accordance with one or more non-limiting embodiments, one or more tests for identifying enhanced activated carbon may be applied to carbon samples such as those produced via the methods discussed herein. One test may be referred to as a dye test. The dye test is a rapid and reproducible method available to identify enhanced carbon materials. In some embodiments, the test may take about three to five hours to complete. The dye test method may also be cheaper and require less instrumentation than conventional methods. In the dye test method, the adsorption of dye over a test period offers a relative quantification of the kinetic performance of the carbon indicating the degree of enhancement. In some embodiments, a dye test as described herein may be used in conjunction with other approaches such as Iodine Number to characterize an enhanced activated carbon.

In accordance with one or more non-limiting embodiments, a method of testing is provided for determining the relative adsorption rate (i.e. mass transfer rate) of unused, reactivated, or spent carbons by adsorption of dye from aqueous solution. In some non-limiting embodiments, the dye may be xylenol orange dye. In other embodiments, the dye may be fluorescein, methylene blue, chlorophyl, or other similar dye. The rate of dye adsorption (in milligrams per gram per square root of hour) by activated carbon using testing conditions similar to those described below is referred to herein as the dye number. The dye number may also be referred to as the intraparticle diffusion rate constant (IDC). Where xylenol orange is used as the dye, the value may be referred to as the xylenol orange number or the xylenol orange intraparticle diffusion constant.

This method may determine or predict how activated carbon will perform in removing dye by adding a known concentration of dye to a known concentration of activated carbon and then measuring the dye concentration remaining in solution as a function of time.

Once completed, the loading rate, known as the dye number, in $mg/g/hr^{1/2}$ is calculated, providing the rate of removal of the adsorbate dye. This method may quantify a carbon's performance under kinetic limitations.

A ground activated carbon sample may be selected. The sample may be selected to substantially fall within a predetermined particle range. For example a range of 325-mesh to 400-mesh carbon may be selected. Sieving may be utilized to select for this range.

The carbon sample may be washed, for example, to improve grain size selection. The carbon sample may be washed with, for example, distilled water and then dried.

A dye solution may be prepared. The dye solution may comprise a dye and a buffer. The dye may be for example xylenol orange. Alternatively, the dye may be another dye having a sufficient absorbance rate so that it is capable of being used with a spectrophotometer. The dye may also be a dye that adsorbs sufficiently slowly so that its rate of adsorption is readily measurable. The dye molarity in the dye solution may be in the range of about 0.01 to 1.0 millimolar (mM). The buffer may be a phosphate buffer. A preferred buffer is one that does not readily adsorb to the carbon so as to alter the adsorption of the dye or compete with the adsorption of the dye.

A dye standard may be prepared comprising the dye and the buffer at a given dye concentration. Samples of the dye standard may be further diluted to prepare samples at varying known concentrations. These varying samples may be used to form a calibration curve. The absorbances of the varying samples may then be separately measured in a spectrophotometer to determine absorbances at a given wavelength. The wavelength may be 487 nm in some non-limiting embodiments. The wavelength may be any wavelength at which the absorption of light shows a local maximum such that the dye concentration can be resolved within the concentration ranges that will be observed during testing. The varying dye concentrations may be, for example, 50, 100, 150, and 200 mg/L.

Figure 9:
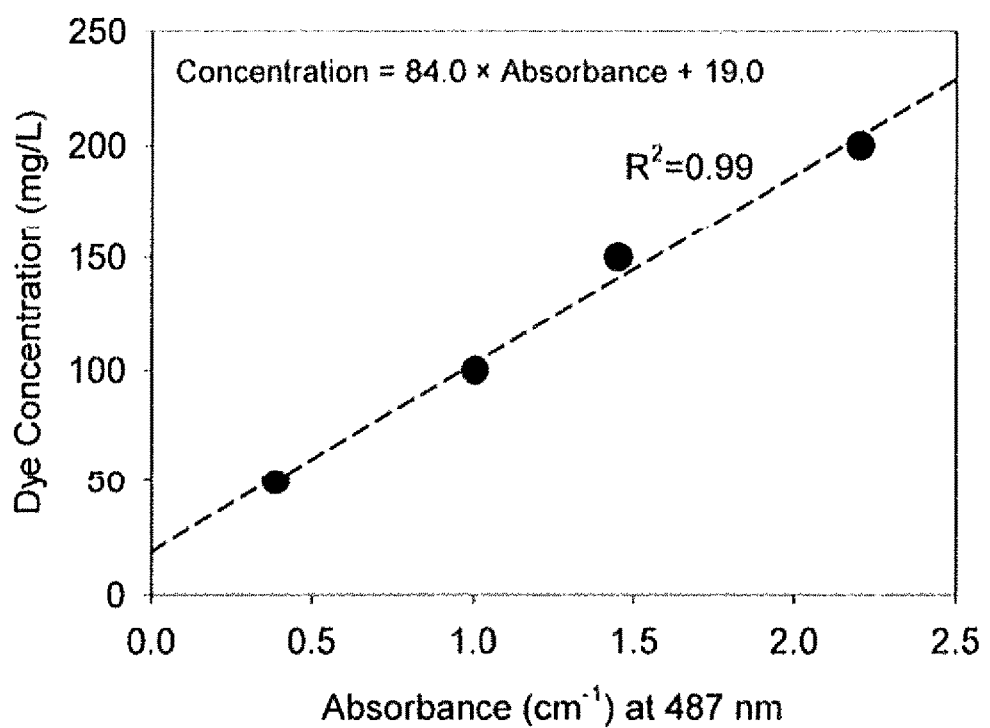

A plot of the sample concentration vs. absorbance may then be assembled. This plot may serve as a calibration curve for further testing involving the dye solution and the carbon sample. FIG. 9 is an example of such a calibration curve, which represents a Xylenol Orange calibration curve at 487 nm.

A sample of the prepared carbon discussed above at a known weight may then be mixed with a known volume of the buffer to form a slurry. After a suitable amount of time has passed allowing for degassing (i.e., wetting) in the carbon pores, a given volume of dye from the dye standard may be introduced to the slurry. After a given amount of time a sample from the slurry may be taken and analyzed in the spectrophotometer at a given wavelength to determine absorbance. Sampling is repeated over given time intervals.

Over time a dye will adsorb to the activated carbon and the concentration of the dye in the solution will be reduced. The concentration of the dye remaining in the solution at the time of sampling may be determined from the absorbance measured by the spectrophotometer in conjunction with the prepared calibration curve. From the concentrations determined above, the dye loading (mg dye/g carbon) may be calculated from the measured absorbance.

If the loading rate vs. the square root of the sample time is plotted then the dye number is the slope of that plotted line.

Figure 10:
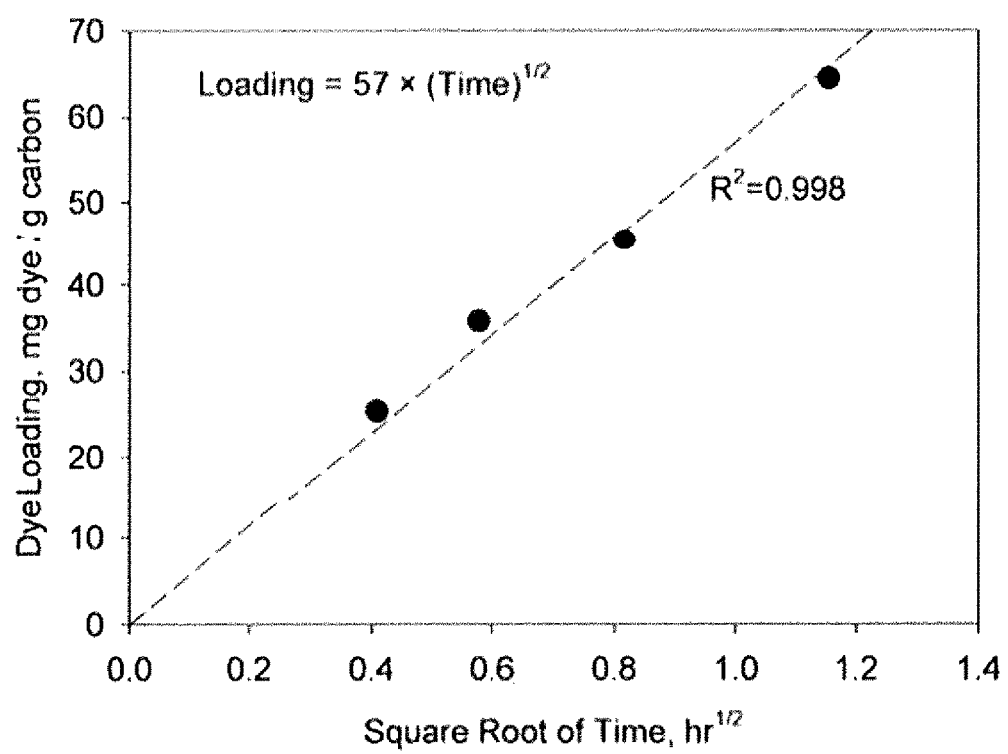

For example, FIG. 10 shows a plot of xylenol orange dye loading versus the square root of elapsed time. The xylenol orange number is determined from the slope of a linear regression through the origin. There, the xylenol orange number is 57 $mg/hr^{1/2}$.

The dye number may be used to predict the performance of an activated carbon in removing contaminants.

In accordance with one or more embodiments, the slope of the dye loading versus square root of time (hours) correlates strongly ($R^2$=0.90-0.99) when combined in a two-variable linear model with Iodine Number (ASTM D4607) as the second variable, to the performance of activated carbon when applied for various removal operations. For example, activated carbons in accordance with various embodiments may be applied for the removal of 2-methylisoborneol removal in surface waters and chlorinated organic removal from groundwater.

Figure 11:
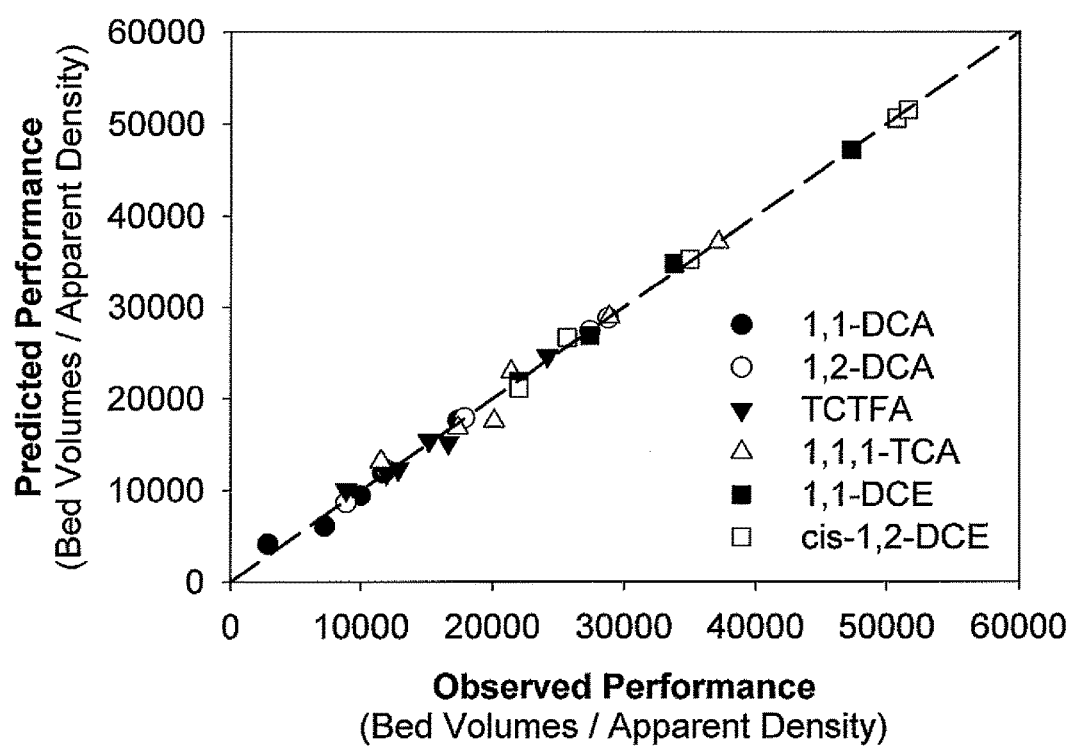

In some non-limiting embodiments, a xylenol orange test number of about 40 $mg/(g*hr^{0.5})$ or greater may generally be indicative of a high-performing activated carbon. The predictive ability of Xylenol Orange Number when combined with Iodine Number (ASTM D4607) in a two-variable linear model is presented in FIG. 11. Shown is the performance for removal of six halogenated organics from groundwater during pilot tests using granular activated carbon. Data points include both direct-activated bituminous, reagglomerated bituminous, coconut, and lignite-based activated carbons. Abbreviations are: 1,1-DCA=1,1-dichloroethane, 1,2-DCA=1,2-dichlorethane, TCTFA=1,1,2-trichloro-1,2,2-trifluoroethane, 1,1-DCE=1,1-dichloroethene, cis-1,2-DCE=cis-1,2-dichoroethene.

Figure 12:
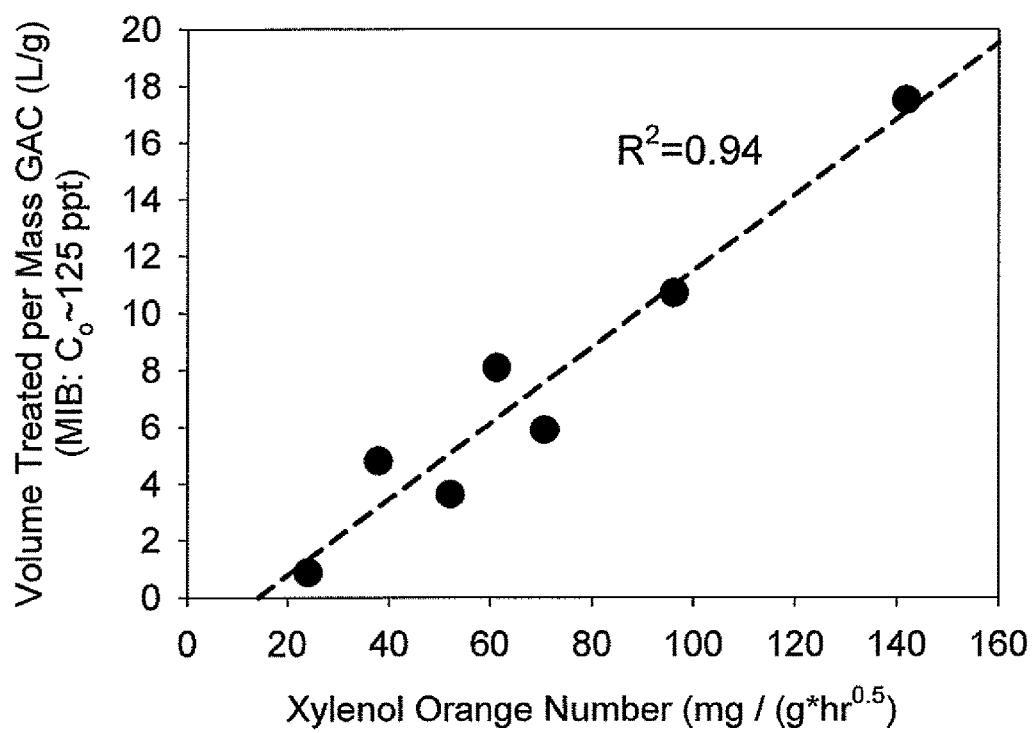

The predictive ability of Xylenol Orange Number for removal of 2-methylisoborneol (MIB) from surface water using coconut-based activated carbons is presented in FIG. 12. Influent MIB concentration was about 125 mg/L. Influent total organic carbon content was 2.2 mg/L. The y-axis shows volume of water treated per mass of activated carbon. Both virgin and reactivated carbons are included as data points. The predictive equations may be determined by a least squares fit to a two variable linear model where that model is:

$$\text{Performance (vol. water treated per mass GAC)} = A^* \text{iodine number (mg iodine/g GAC)} + B^* \text{dye number (mg dye/g GAC/hour)}$$

The predictive ability is further discussed in reference to Example 11 below.

With characterization methods, such as the dye test disclosed herein, that may be made readily accessible to the activated carbon consumer, the consumer has a means to predict the performance of carbons for a desired application. By first building a knowledge base that includes the relative value of dye number and iodine number the consumer can select carbons that will offer the greatest value and most favorable performance. Heretofore the consumer did not have a method for readily characterizing the mass transfer limitations of a given carbon and could only base selection on iodine number and/or mechanical properties (e.g. apparent density and abrasion number). With the dye number in-hand the consumer can usefully quantify the two main properties that control carbon performance: 1) adsorption capacity (via iodine number) and 2) adsorption kinetics (via dye number).

The function and advantages of these and other embodiments will be more fully understood from the following examples. The examples are intended to be illustrative in nature and are not to be considered as limiting the scope of the systems and methods discussed herein.

EXAMPLE 1

Mesoporous coconut shell-based activated carbon was produced in accordance with one or more embodiments. About 8 g to about 12 g of coconut shell-based activated carbon was treated. More specifically, about 9 g to about 11 g of coconut shell-based activated carbon was treated. About 0.1% to about 5% w/w Ca was used to catalyze the coconut shell-based activated carbon. More specifically, about 0.5% to about 2.0% w/w Ca was used. About 0.15 gal/lb GAC to about 0.3 gal/lb GAC was used. Specifically, about 0.2 gal/lb GAC to about 0.25 gal/lb GAC may be used.

The following specific materials were used:
10 g AquaCarb1240C® granular activated carbon, (2% moisture).
Citric Acid (anhydrous)
Calcium Chloride (anhydrous)
The following assumptions and principles were used:
AC1240C® granular activated carbon was mixed with 1% w/w Ca.
0.225 gal solution/lb GAC.
The following calculations were used:

Mass of $CaCl_2$
$$\left(\frac{10 \text{ g } GAC}{\text{batch}}\right)\left(\frac{0.01 \text{ g Ca}}{\text{g } GAC}\right)\left(\frac{1 \text{ mol Ca}}{40.08 \text{ g Ca}}\right)$$
$$\left(\frac{1 \text{ mol } CaCl_2}{1 \text{ mol Ca}}\right)\left(\frac{110.98 \text{ g } CaCl_2}{\text{mol } CaCl_2}\right) = 0.28 \text{ g } CaCl_2$$

Mass of $C_6H_8O_7$
$$\left(\frac{10 \text{ g } GAC}{\text{batch}}\right)\left(\frac{0.01 \text{ g Ca}}{\text{g } GAC}\right)\left(\frac{1 \text{ mol Ca}}{40.08 \text{ g Ca}}\right)$$
$$\left(\frac{2 \text{ mol } C_6H_8O_7}{1 \text{ mol } Ca^{2+}}\right)\left(\frac{192.12 \text{ g } C_6H_8O_7}{\text{mol } C_6H_8O_7}\right) = 0.96 \text{ g } C_6H_8O_7$$

Volume of $H_2O$
$$\left(\frac{10 \text{ g } GAC}{\text{batch}}\right)\left(\frac{1 \text{ lb}}{454 \text{ g}}\right)\left(\frac{0.225 \text{ gal}}{\text{lb}}\right)\left(\frac{3785 \text{ mL}}{\text{gal}}\right) = 18.8 \text{ mL}$$

GAC was soaked in solution for about 12 hours. Liquid was then removed by vacuum filtration. Without drying, material was heated to about 300° C. in $N_2$ (approximately 17 cc/min/g GAC) (or similarly inert atmosphere). With $N_2$ flow continuing, the GAC was heated in steam (0.01 to 0.2 mL/min/g GAC) from 300° C. to pyrolysis temperature (about 800° C. to about 1000° C.). Heating at pyrolysis temperature was continued until a desired mass loss was achieved, typically 10% as a minimum and 15% as an optimum. In some embodiments, maximum may be about 30% as particles lose integrity. In some embodiments, mass loss rate may largely be dependent upon the steam rate. The material was then cooled as rapidly as possible with steam/$N_2$ flow continuing.

Figure 2:
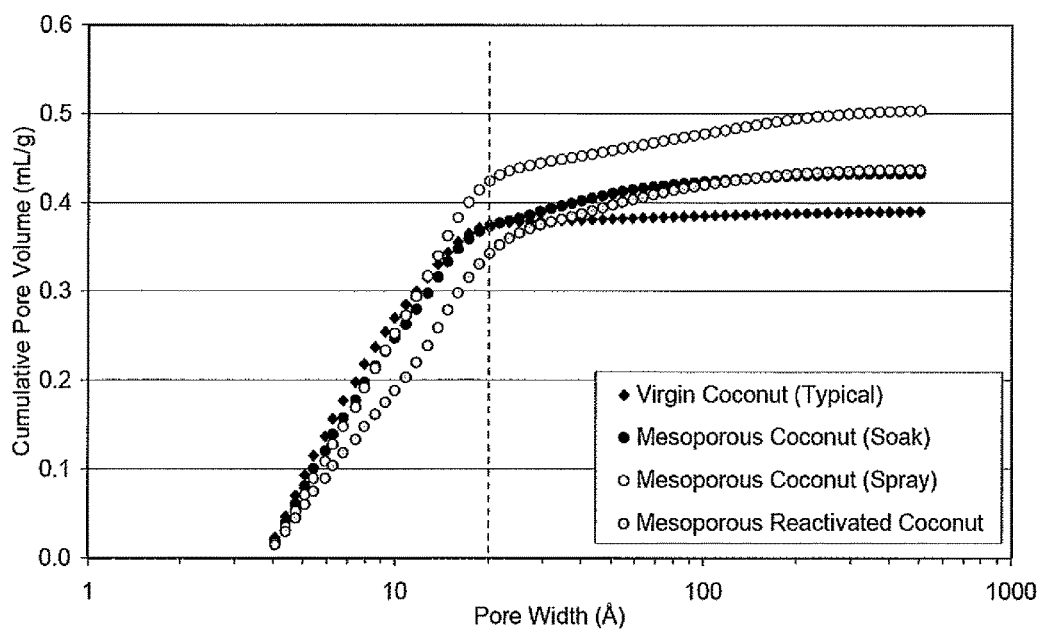

Discrete data relating to pore volume distribution for activated carbon produced in accordance with one or more embodiments disclosed herein is presented in FIG. 1. Bituminous relates to F400 activated carbon, commercially available from Calgon®, which generally has fewer micropores and significantly more mesopores than the AquaCarb 1240C® starting material used in this Example. Reactivated Coconut relates to a spent coconut shell-based activated carbon that was commercially reactivated. Mesoporous Coconut and Mesoporous React. Coconut relate to activated carbon produced with one or more of the embodiments disclosed herein. Corresponding cumulative data relating to pore volume distribution is presented in FIG. 2. FIGS. 1 and 2 were produced from argon adsorption isotherms where the isotherm data has been reduced using the density functional theory (DFT). Both the cumulative and discrete representations of the pore volume indicate that mesopores were formed in the activated carbon during treatment as per the embodiments disclosed herein while micropore volume was mostly maintained during those treatments.

EXAMPLE 2

A target application is removal of disinfection by-products from treated drinking water and as such chloroform can be used to represent the larger class of trihalomethanes. Rapid small-scale column tests (RSSCTs, ASTM D6586) were performed to assess chloroform removal performance of the GAC produced in accordance with one or more of the disclosed emodiments. For these RSSCTs, chloroform was spiked to a level of 90 µg/L in a natural groundwater; RSSCTs were scaled to represent a full-scale bed operating at a 5 minute empty-bed contact time using 12×40 US mesh full-size grains. Effluent chloroform concentrations were measured for about 16,000 bed volumes, corresponding to approximately 2 months of full-scale service.

Figure 3:
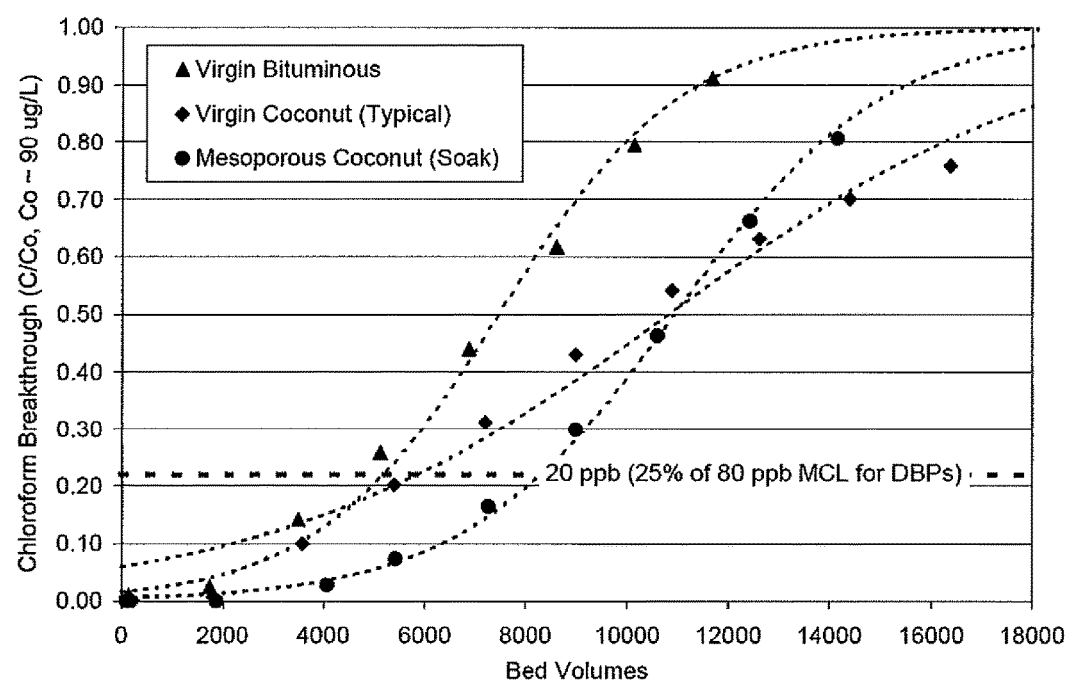

FIG. 3 presents chloroform breakthrough data in the groundwater as measured in RSSCTs. The results indicate that the mesoporous activated carbon produced in accordance with one or more embodiments provided 40% longer bed life than the virgin material and about 65% longer bed life than the F400 product in a natural groundwater containing competing background organics at a level of 0.5 mg/L TOC.

EXAMPLE 3

Mesoporous coconut shell-based activated carbon was produced with a soak method in accordance with one or more embodiments. 192.5 gallons of 50% w/w citric acid solution was added to 2729 gallons of water. 80 gallons of 32% w/w CaCl2 was added to the citric acid/water solution. The resulting solution was then added to 10,000 lb virgin 12×30 US Mesh granular coconut shell-based activated carbon. The activated carbon was allowed to soak in the solution for 12 hours. The solution was then drained from the activated carbon. The activated carbon was heated to 950° C. in the presence of steam at an application rate of 1 lb steam/lb activated carbon.

Mesoporous coconut shell-based activated carbon was separately produced with a spray method in accordance with one or more embodiments. 74 mL of 50% w/w citric acid solution was added to 222 mL of water to produce 15.6% w/w citric acid solution. 13.2 g CaCl2 was added to the 15.6% w/w citric acid solution. 98.7 g of the resulting solution was applied as a fine mist to a 1 mm thick layer of 307 g virgin 12×40 US Mesh granular coconut shell-based activated carbon. The activated carbon was then dried for 1 hr at 32° C. and then heated to 100° C. for 1 hr. The temperature was then ramped to 930° C. and held for 1 hr. The activated carbon was cooled in steam to room temperature.

EXAMPLE 4

RSSCTs were conducted for the removal of 2-methylisoborneol (MIB) from clarifier effluent at a drinking water treatment utility. These tests simulated the full-scale operation of existing GAC beds at the treatment facility (Table 1). RSSCT test operation was based on ASTM Method D-6586.

TABLE 1

Dimensions and operating parameters for RSSCTs.

|  | Full-Scale |  | Small-Scale |  |
|---|---|---|---|---|
| Influent MIB | 120 | ng/L, max | 125 | ng/L |
| Bed Depth | 54 | in | 2 | cm |
| Flow | 1.5 | mgd | 6-10 | mL/min |
| Area | 365 | ft2 | 0.32 | cm2 |
| EBCT | 11.8 | min | 3.6 | s |
| Grain Size | 8 × 30 (1.49) | US Mesh (mm) | 170 × 200 | US Mesh |
|  | 12 × 30 (1.14) |  | 0.081 | mm |

Throughout testing the influent water temperature was maintained at 54° F. (12° C.). The MIB concentration in tests was based on the highest level experienced at the treatment plant during a taste and odor episode. Performance in the RSSCTs thus indicates the GACs' ability to perform under strained conditions. The natural organic matter content of the test sample was about 3.0 mg/L, measured as total organic carbon (TOC).

Figure 4:
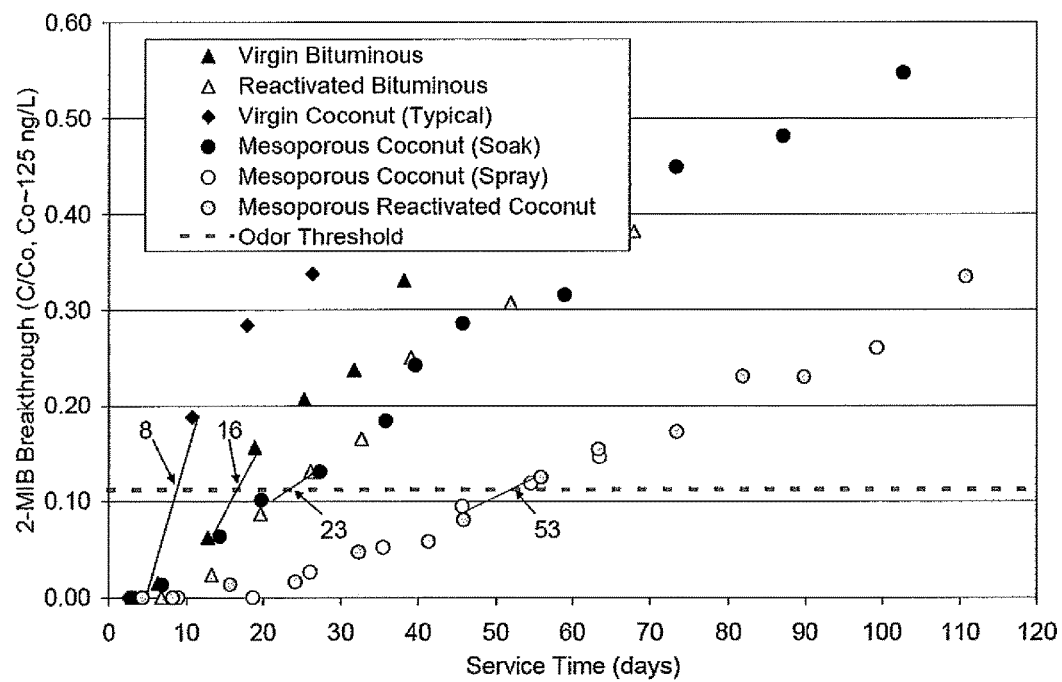

Performance was measured in terms of simulated service time provided until the effluent reached the human odor threshold of 14 ng/L. FIG. 4 presents breakthrough data of 2-methylisoborneol as simulated in RSSCTs. Values shown with arrows indicate number of service days until effluent concentration exceeds odor threshold of 14 ng/L. Both mesoporus coconut shell-based GACs in accordance with one or more embodiments provided about 53 days of service time until reaching this threshold. The bituminous coal-based GACs provided about 16 to about 23 days of service time. The typical virgin coconut shell-based GAC provided 8 days of service time. The data indicates that mesoporous coconut shell-based GACs in accordance with one or more embodiments would allow the utility to reach almost two months of service time during a taste and odor event.

EXAMPLE 5

RSSCTs were conducted to determine the effectiveness and efficiency of typical virgin coconut shell-based GAC versus mesoporous coconut shell-based GAC for removing a select set of chlorinated organic compounds. These compounds had been identified historically in a groundwater source. Tetrachloroethylene (PCE), carbon tetrachloride (CTC), and 1,2,3-trichloropropane (TCP) were dosed to historical concentrations; trichloroethylene (TCE) and chloroform were present in the as-received water and were not dosed additionally. Chloroform was apparently present only in the post-spike (i.e. test influent) water; it may have been present in the as-received water however preliminary testing did not screen for this compound.

Compounds Examined in RSSCTs:

| Compound | As-Filtered Water for RSSCT (ug/L) | Avg. Post-Spiking for RSSCT (ug/L) |
|---|---|---|
| carbon tetrachloride (CTC) | 1.4 | 2.7 |
| tetrachloroethylene (PCE) | 1.9 | 5.2 |
| 1,2,3-trichloropropane (TCP) | 0.17 | 0.410 |
| trichloroethylene (TCE) | 1.8 | 1.5 |
| chloroform | — | 0.67 |

Testing was conducted according to ASTM Standard Test Method D-6586-03, the Prediction of Contaminant Adsorption on GAC in Aqueous Systems Using Rapid Small-Scale Column Tests. RSSCT columns were designed to simulate the full-scale operation of a single 12 foot diameter, 30,000 lb GAC adsorber at 1000 gpm. Small-scale columns were constructed of polycarbonate with stainless steel fittings, PTFE tubing, and stainless steel influent vessels.

Vessel/Column Operating Parameters:

|  | Full-Scale |  | Small-Scale |  |
|---|---|---|---|---|
| Flow Rate | 1000 | gpm | 23.9 | mL/min |
| Fill Weight | 30,000 | Lb | 0.518 | g |
| Bed Depth (varies w/AD) | 10.5 | ft | 6.0 | cm |
| Bed/Column Diameter | 12 | ft | 0.48 | cm |
| Hydraulic Loading Rate | 8.8 | gpm/ft$^2$ | 33 | gpm/ft$^2$ |
| Particle Size | 12 × 30 | US Mesh | 170 × 200 | US Mesh |

To best replicate the conditions that would be observed on site (e.g. background organics) the RSSCTs were conducted with a sample of the natural water. To prepare this water for the RSSCTs it was filtered through a 0.2 μm absolute-rate Flotrex cartridge (Osmonics, Inc.) to remove any suspended solids. Thereafter, contaminants were spiked concurrently using standard mixtures (5000 μg/mL) of the compounds dissolved in methanol (Supelco, Bellefonte, Pa.). After spiking the filtered site water with the target contaminants, the water was held at about 2 to about 4° C. for the duration of the test and kept under about 4 psi of nitrogen gas. This procedure aimed to minimize the volatilization of the contaminants during the about 48 hour RSSCT duration.

Influent and effluent samples were analyzed according to the California Department of Public Health Modified USEPA Method 524.2 for TCP and by the standard USEPA Method 524.2 for all other chlorinated organics. By this approach reporting limits for TCP analysis were 0.005 μg/L and 0.5 μg/L for CTC, PCE, TCE, and chloroform.

Figure 5:
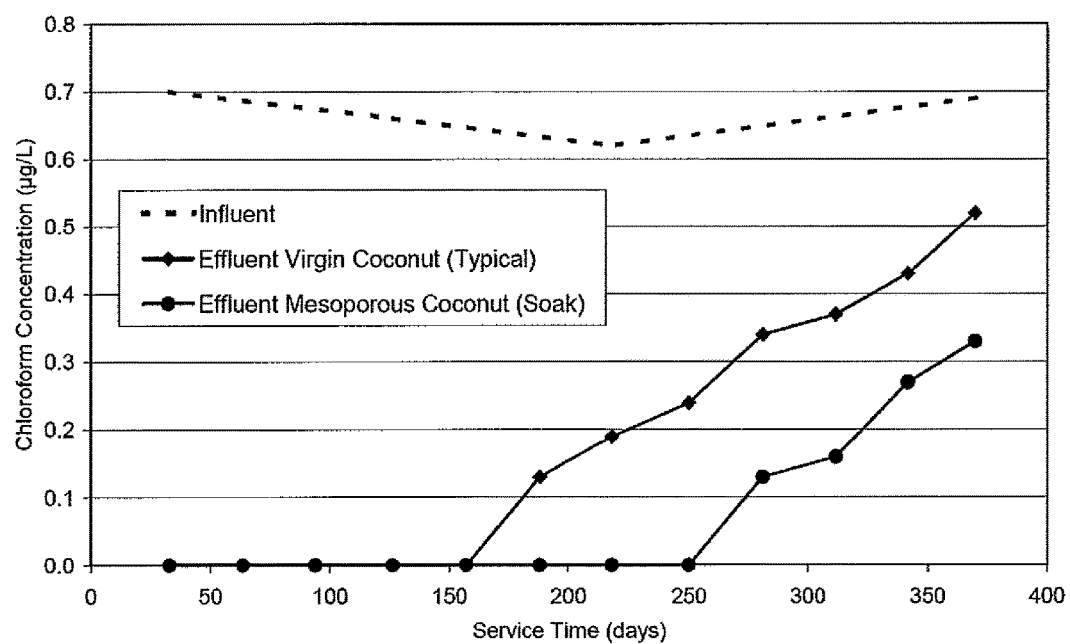

The RSSCTs simulated the contaminant removal that would be observed at up to 370 days of service time. FIG. 5 presents breakthrough data of chloroform from groundwater as measured in RSSCTs. During this period only chloroform breakthrough was observed above the method detection limit (MDL). For virgin coconut shell-based GAC, chloroform was detected at 160 days of service life. For mesoporous coconut shell-based GAC in accordance with one or more embodiments, chloroform was detected at 250 days of service life. This represents a 56% improvement in service life to detection.

EXAMPLE 6

RSSCTs were conducted to measure the performance of mesoporous coconut shell-based GAC and virgin coconut shell-based GAC 1230C (AC1230C), versus a reagglomerated bituminous coal-based GAC. The compounds of interest for this testing were a select set of chlorinated organics and these had been identified historically in the influent groundwater at the site.

Compounds Examined in RSSCTs

| Compound | As-Filtered Water for RSSCT (ug/L) | Average Post-Spiking for RSSCT (ug/L) |
|---|---|---|
| 1,1-dichloroethene (1,1-DCE) | 0.99 | 1.81 |
| 1,1-dichloroethane (1,1-DCA) | 3.21 | 3.74 |
| cis-1,2-dichloroethene (cis-1,2-DCE) | 0.25 | 1.13 |
| 1,1,1-trichloroethane (1,1,1-TCA) | 0.70 | 0.92 |
| Trichloroethene (TCE) | 1.94 | 10.38 |
| Tetrachloroethene (PCE) | 0.62 | 0.62 |

Testing was conducted according to ASTM Standard Test Method D-6586-03, the Prediction of Contaminant Adsorption on GAC in Aqueous Systems Using Rapid Small-Scale Column Tests. RSSCT columns were designed to simulate the full-scale operation of the existing vessels. Columns were constructed of polycarbonate with stainless steel fittings, PTFE tubing, and stainless steel influent vessels.

Vessel/Column Operating Parameters:

| | Full-Scale | | Small-Scale | |
|---|---|---|---|---|
| Flow Rate | 510 | gpm | about 58 | mL/min |
| Fill Weight | 17,000 | Lb | 1.68 | g |
| Bed Depth | 7.1 | ft | 17.5 | cm |
| Column Diameter | 10 | ft | 0.48 | cm |
| Hydraulic Loading Rate | 6.5 | gpm/ft$^2$ | 80 | gpm/ft$^2$ |
| Particle Size | 12 × 40 | US Mesh | 170 × 200 | US Mesh |

RSSCTs were conducted with a sample of groundwater obtained directly from a municipal well. In preparation for the RSSCT this water was passed through a 0.2 μm Flotrex filter (Osmonics, Inc.) to remove any suspended solids. The contaminants were spiked to representative concentrations using standard mixtures (1000-5000 μg/mL) of the 5 target compounds dissolved in methanol (Supelco, Bellefonte, Pa.). After spiking the filtered site water with the target contaminants, the water was held at 4° C. for the duration of the test and kept under about 5 psi of nitrogen gas. Effluent temperature for both columns was consistently about 13° C. to about 14° C.

Influent and effluent samples were analyzed according to USEPA Method 524.2 for volatile organic compounds. By this approach detection limits were 0.3-0.5 μg/L. The background TOC concentration of the as-received groundwater was also measured and the average of 5 samples was 0.2 mg/L.

The RSSCTs for virgin coconut and virgin bituminous were able to simulate full-scale results that would be observed at up to 180 days of service time. The RSSCT for mesoporous coconut was extended to simulate 330 days of service time as breakthrough did not begin to occur until about 180 days. During this period, only breakthrough of 1,1-DCA was observed. The breakthrough of other influent contaminants was not observed during this period and all concentrations were non-detect in effluent samples.

Initial breakthrough (above the detection limit of 0.4 μg/L) for virgin bituminous occurred at 11,800 bed volumes (BV) and breakthrough continued steadily thereafter, reaching 95% of the influent concentration by about 31,000 BV. For virgin coconut breakthrough was first observed with the sample at 23,500 BV and by about 31,000 BV breakthrough had reached 42% of the influent concentration. Breakthrough was first observed with mesoporous coconut at about 32,000 BV and reached 75% of the influent concentration at about 53,000 BV.

By fitting a mathematical curve to the data points (gray short-dashed lines) the length of each mass transfer zone (MTZ) could be calculated as described in the ASTM RSSCT method. As such, the expected full-scale MTZ length for mesoporous coconut would be 3.2 feet versus a length of 3.8 feet for virgin coconut and 4.5 feet for virgin bituminous. The MTZ length of mesoporous coconut indicates the adsorption rate was about 30% faster than virgin bituminous during adsorption of 1,1-DCA.

Figure 6:
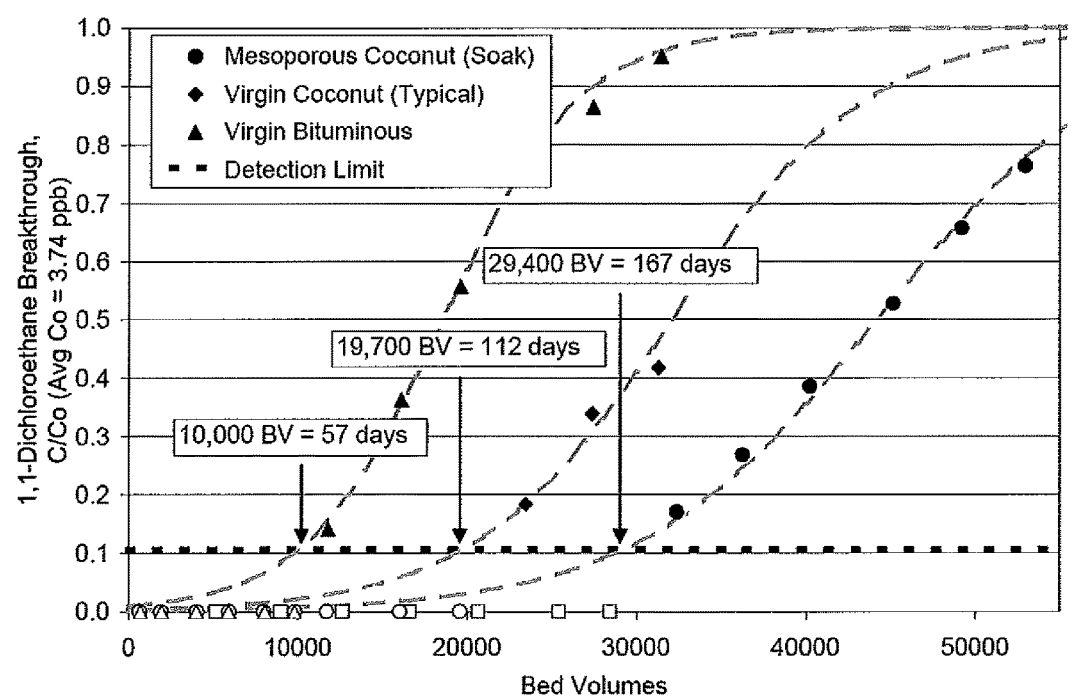

FIG. 6 presents breakthrough data of 1,1-dichloroethane (1,1-DCA) versus bed volumes as measured in RSSCT comparing Mesoporous Coconut and Virgin Coconut to reagglomerated Virgin Bituminous GAC. Data was used to estimate a full shape of the breakthrough curve (short dashed lines). Detection limit for 1,1-DCA is also shown (long dashed lines). Data points shown in white were non-detect at this limit.

From the fit curve it could be estimated also that breakthrough of 0.4 μg/L 1,1-DCA occurred at about 10,000 BV for virgin bituminous, about 19,700 BV for virgin coconut, and about 29,400 BV for mesoporous coconut. As a general conclusion, when applied at a full-scale about 8.2 minute empty-bed contact time mesoporous coconut would be expected to provide 167 days of service life to breakthrough of 1,1-DCA. Under the same conditions, virgin coconut would be expected to provide 112 days of service life, and virgin bituminous 57 days of service life. Therefore the use of mesoporous coconut would provide a about 200% improvement in bed life over virgin bituminous and about 50% improvement over virgin coal.

EXAMPLE 7

A target application is removal of pesticides from water and as such ethylene dibromide (EDB) can be used to represent the larger class of halogenated pesticide compounds. RSSCTs (ASTM D6586) were performed to assess EDB removal performance of the GAC produced in accordance with one or more of the disclosed embodiments. For these RSSCTs, EDB was spiked to a level of 300 ng/L in a natural groundwater supply, RSSCTs were scaled to represent a full-scale bed operating at a 5 minute empty-bed contact time using 12×40 US mesh full-size grains. Effluent EDB concentrations were measured for about 70,000 bed volumes, corresponding to approximately 8 months of full-scale service.

Figure 7:
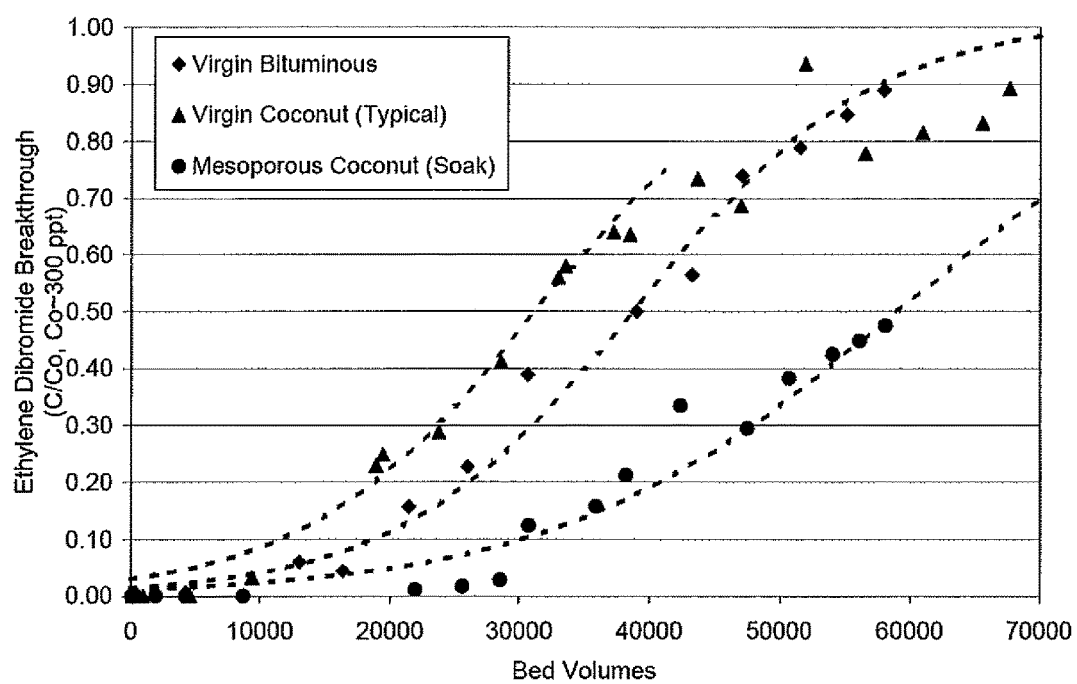

FIG. 7 presents ethylene dibromide breakthrough data in the groundwater as measured in RSSCTs. The results indicate that the mesoporous activated carbon produced in accordance with one or more embodiments provided 90% longer bed life (59,000 bed volumes) to 50% breakthrough than the virgin material (31,000 bed volumes) and about 50% longer bed life (39,000 bed volumes) than the bituminous product in a natural groundwater containing competing background organics at a level of 0.5 mg/L TOC.

EXAMPLE 8

A set of RSSCTs was conducted with surface water to compare total organic carbon (TOC) removal between the reactivated bituminous-based granular activated carbon (GAC) and reactivated mesoporous coconut shell-based GAC. These tests simulated the full-scale operation of existing GAC vessels. RSSCT test operation was based on ASTM Method D-6586 and modified for proportional diffusivity scaling which applies to simulating the removal of large organic compounds. Influent and effluent samples were analyzed for total organic carbon (TOC) concentration.

Full-Scale dimensions and operating parameters that were simulated in the RSSCTs:

| Carbon Type | Reactivated Mesoporous Coconut | Reactivated Bituminous | |
|---|---|---|---|
| Grain Size | 12 × 30 | 8 × 30 | US Mesh |
| Apparent Density | 0.47 | 0.53 | g/mL |
| Backwashed Density | 0.43 | 0.49 | g/mL |
| Weight/Adsorber | 35,500 | 40,000 | lb |
| Adsorber Diameter | 12 | | ft |
| Flow/Train | 463 | | gpm |
| Area | 113 | | sq ft |
| Hydraulic Loading | 4.1 | | gpm/sq ft |
| Empty-Bed Contact Time | 23.7 | | min |

Small-Scale dimensions and operating parameters of RSSCTs:

| Carbon Type | Reactivated Mesoporous Coconut | Reactivated Bituminous | |
|---|---|---|---|
| Grain Size | 200 × 400 | | US Mesh |
| Bed Depth | 11.4 | 8.8 | cm |
| Bed Volume | 2.0 | 1.6 | mL |
| Weight/Column | 0.91 | 0.85 | g |
| Flow | 2.0 | | mL/min |
| Column Diameter | 0.48 | | cm |
| EBCT | 1.02 | 0.78 | min |

Figure 8:
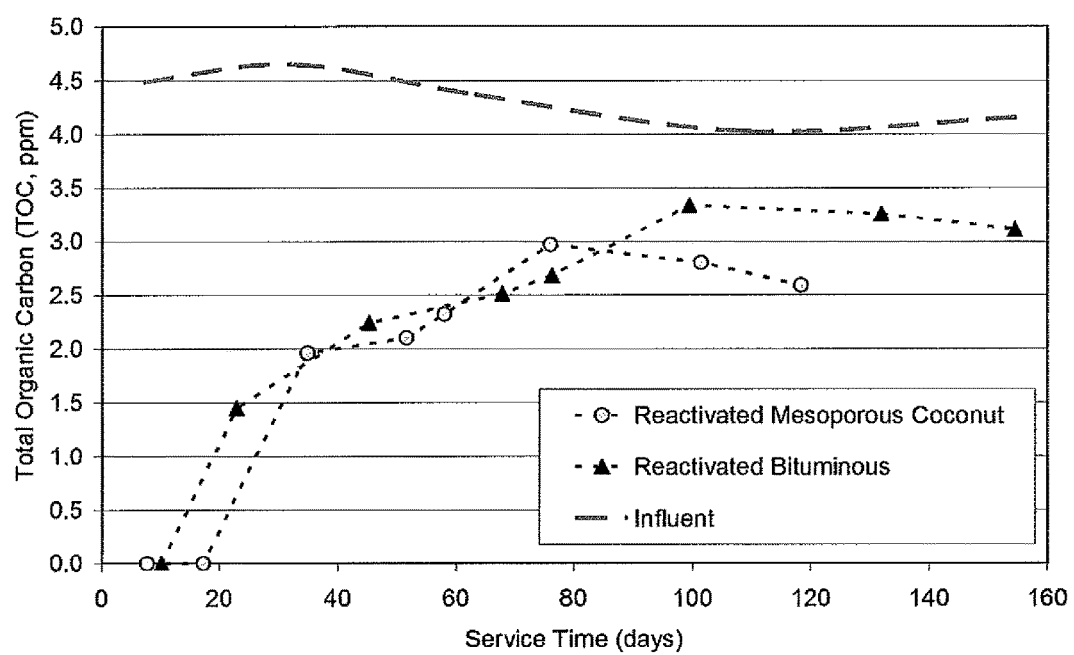

FIG. 8 presents breakthrough data of organic compounds measured as Total Organic Carbon (TOC) in the surface water as measured in RSSCTs. Reactivated mesoporous coconut provided about 7 days longer service life to an effluent of about 1.5 ppm TOC. Above 1.5 ppm, the reactivated mesoporous coconut matches the performance of reactivated bituminous. A typical coconut shell-based GAC would be expected to show near-immediate TOC breakthrough due to its solely microporous nature.

EXAMPLE 9

In accordance with one or more embodiments, a protocol for performing a dye test is provided. This method determines how activated carbon will perform when removing the dye xylenol orange by adding a known concentration of dye to a known concentration of activated carbon and then measuring the dye concentration remaining in solution as a function of time. Once completed, the loading rate in mg/g/hr$^{1/2}$ is calculated, providing the rate of removal of the adsorbate Xylenol Orange. This method quantifies a carbon's performance under kinetic limitations. The loading rate in mg/g/hr$^{1/4}$ is reported as the xylenol orange number.

This test method covers the determination of the relative adsorption rate (i.e. mass transfer rate) of unused or reactivated carbons by adsorption of xylenol orange from aqueous solution.

As a first step activated carbon is prepared. Proper GAC sampling (Practice E300) and preparation (grinding, classification, and washing) are required for reproducible results. A sieve nest is constructed with a top cover, a 325-mesh sieve, a 400-mesh sieve, and a receiver pan. The ground carbon sample is added to the upper sieve (325-mesh) and the sieve nest is then placed on the sieve shaker for several minutes.

The above step is repeated until a sufficient quantity (~0.1 g dry) of ground GAC can be recovered from the 400-mesh sieve. Ground sample on the 325-mesh sieve is washed through to the 400-mesh sieve using reagent grade water. This step is continued until the water passing the 325-mesh sieve appears clear.

Sample collected on the 400-mesh sieve is washed with distilled water until the water passing the sieve appears clear. Approximately 5-10 L of reagent water is required for this. Sample remaining on the 400-mesh sieve is then washed into a ceramic drying dish. The sample should be allowed to settle for 1 minute and then decanted, removing any particles that float or do not readily settle. This step should be repeated until the supernatant appears clear (approximately 3 times).

The drying dish is covered with foil and dried according to ASTM D 2867 (150±5° C. for 3 h). The dry carbon should be cooled to room temperature and stored in a dessicator until use. The prepared sample, when shaken in a clear glass container, should produce little to no visible dust.

Next, solutions are prepared. For a 10 mM, pH 7.2 phosphate buffer solution, measure out 0.379 gram of sodium phosphate monobasic anhydrous and 0.964 gram of sodium phosphate dibasic anhydrous and add these to 1 liter of reagent water. Mix the solution until no solids are visible to the naked eye. The buffer solution must be prepared monthly to ensure consistent results.

A xylenol orange dye standard is prepared at 2200 mg/L by adding 440 mg of dye to 200 mL of phosphate buffer. Stir solution for at least one hour then store in a brown glass bottle in a cool dark area. The dye standard must be prepared monthly to ensure consistent results.

A calibration curve is prepared from the xylenol orange dye standard. This curve will be used to calculate the concentration of the samples taken during the dye test after the sample has been passed through a 0.1 micron syringe filter to separate the dye from the carbon. A small amount of dye will be lost in the syringe filters during filtration and the calibration curve must account for this lost dye.

The 2200 mg/L xylenol orange standard is diluted with phosphate buffer to four selected concentrations of 50, 100, 150, and 200 mg/L using the volumes listed in the table below:

| Concentration (mg/L) | Flask Size (mL) | Dye to add (mL) |
|---|---|---|
| 50 | 10 | 0.227 |
| 100 | 10 | 0.455 |
| 150 | 10 | 0.682 |
| 200 | 10 | 0.909 |

2 mL of each concentration are pipetted into separate 5 mL syringes fitted with 0.1 micron syringe tip filters. The syringes are then emptied into separate cuvettes. The spectrophotometer is zeroed using a cuvette containing only the phosphate buffer solution and thereafter each the absorbance of each sample is measured at a wavelength of 487 nm. The absorbance (cm$^{-1}$) is recorded to three decimal places.

Measurement of the standards should be completed within 20 minutes of preparation to ensure that values do not change due to evaporation. Consult the manufacturer's recommendation for the pre-analysis warm-up time required for the specific spectrophotometer.

A plot of the standard concentration (mg/L) vs. absorbance ($cm^{-1}$) is created as shown in FIG. 9, which shows a xylenol orange calibration curve at 487 nm. (The curve does not intersect the origin because some dye is adsorbed in the syringe filter.) A linear fit to the filtered curve points must produce a coefficient of determination ($R^2$) of 0.98 or greater. If the $R^2$ does not meet these limits, the calibration must be repeated.

A new standard curve should be prepared for any change in reagents or materials, i.e. cuvette or syringe filter lot numbers.

Next, a dye test is performed. To begin, 50 mL of phosphate buffer solution are added to a 100 mL beaker. The beaker is placed on a stir plate and a stir bar is added to the beaker. A sample of 325×400-mesh carbon is weighed to 0.0500+−0.0005 grams and added to the 50 mL of phosphate buffer solution. The stir plate is started and set to a rate sufficient to suspend the carbon sample completely. The slurry of carbon and phosphate buffer is covered with a watch glass to ensure minimal evaporation during the test. The carbon and phosphate buffer solution are allowed to mix for at least 20 minutes. This ensures that the carbon pores are degassed and will be accessible to the dye during the test.

Once 20 minutes has elapsed, 5.00 mL of dye from the 2200 mg/L solution are added to the slurry using a 1-10 mL pipette. The test timer is started immediately once the dye has been fully added to the slurry.

At four sample times (10 min., 20 min., 40 min., 80 min.), 2 mL of slurry are collected from the carbon/dye solution and are pipetted into syringes equipped with 0.1 micron filters. The syringes are then emptied into cuvettes. A small amount of liquid will remain in the syringe filter, but there should be no liquid left in the syringe after emptying them into the cuvettes. After each sample is taken it should be analyzed within 5 minutes.

The spectrophotometer is zeroed (as it was for the calibration curve) and each sample is analyzed at a wavelength of 487 nm. The absorbance is recorded to 3 decimal places.

Next calculations are performed to determine the dye number for the carbon. Using the equation obtained for the calibration curve produced above, the concentration in mg/L from the absorbance obtained is calculated as follows:

$$C = m*A + b$$

Where:
C=concentration of dye, mg/L
m=slope of calibration curve, cm·mg/L
A=absorbance of sample at 487 nm,
b=y-intercept of calibration curve, mg/L From the concentrations determined in the above equation, the dye loading (mg dye/g carbon) may be calculated as follows:

$$Q_{T2} = (C_{T1} - C_{T2})*(V_{T1}/M_{T1})*(L/1000 \text{ mL})$$

Where:
$Q_{T2}$=dye loading at end of sampling period, mg/g
$C_{T1}$=concentration of dye at start of sampling period, mg/L
$C_{T2}$=concentration of dye at end of sampling period, mg/L
$V_{T1}$=volume of solution at start of sampling period, mL
$M_{T1}$=mass of carbon at start of sampling period, g For each sample point, 2 mL is removed from the solution volume, and with that volume, about 0.02 g of carbon is assumed to be removed; these reductions must be accounted for with each subsequent loading calculation.

The table below shows these values.

| Sample Time (min) | Remaining Carbon ($M_{T1}$, g) | Remaining Solution ($V_{T1}$, mL) |
|---|---|---|
| 10 | 0.0500 | 55.00 |
| 20 | 0.0481 | 53.00 |
| 40 | 0.0462 | 51.00 |
| 80 | 0.0442 | 49.00 |

The loading rate vs. the square root of the sample time is plotted for each carbon. Time should be converted from minutes to hours for this plot, as shown in FIG. 10. A linear fit through the origin must produce an $R^2$ of 0.95 or greater, or the test should be repeated.

From the linear regression of the loading data through the origin the xylenol orange number can be determined as follows:

$$Q_t = M_{XON} * t^{1/2}$$

Where:
$Q_t$=dye loading at time (t), mg/g
t=elapsed time, hr
$M_{XON}$=xylenol orange number, mg/g/$hr^{1/2}$ FIG. 10 shows a plot of xylenol orange dye loading versus the square root of elapsed time. The xylenol orange number is determined from the slope of a linear regression through the origin. Here the xylenol orange number is 57 mg/g/$hr^{1/2}$.

EXAMPLE 10

Dye testing was performed on six different coconut based activated carbon samples using Xylenol Orange according generally to the testing protocols described above.

Figure 13:
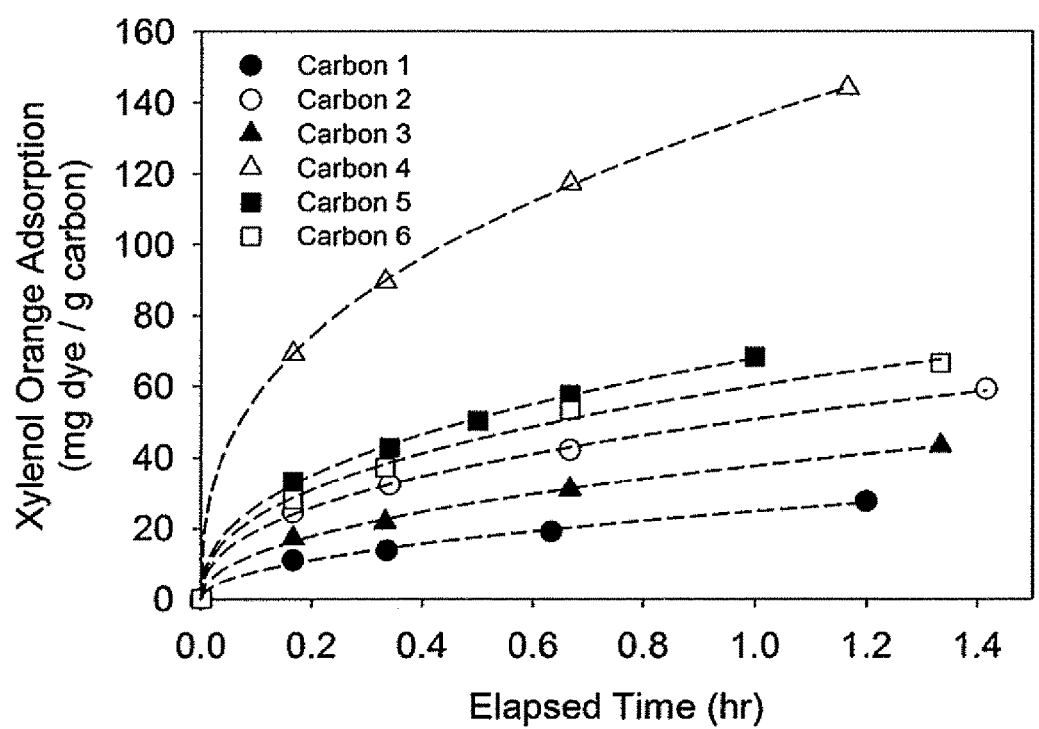

For example, FIG. 13 shows a graph of the adsorption of the dye, Xylenol Orange, versus the elapsed test time for six different carbon sources. Initial dye concentration is 200 mg/L and initial carbon dosage is 0.05 g.

Figure 14:
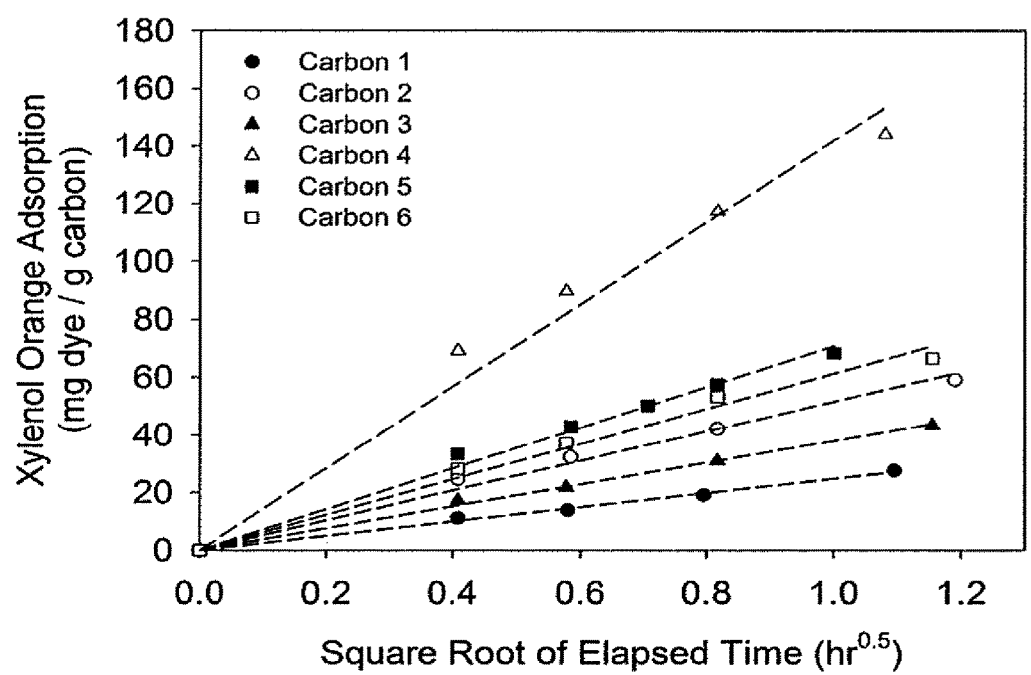

The time data were then converted to create a graph showing adsorption of the dye, Xylenol Orange, versus the square root of elapsed test time, as shown in FIG. 14. The slope of the linear correlation indicates the intraparticle diffusion constant (IDC) for each of the carbon types.

Figure 15:
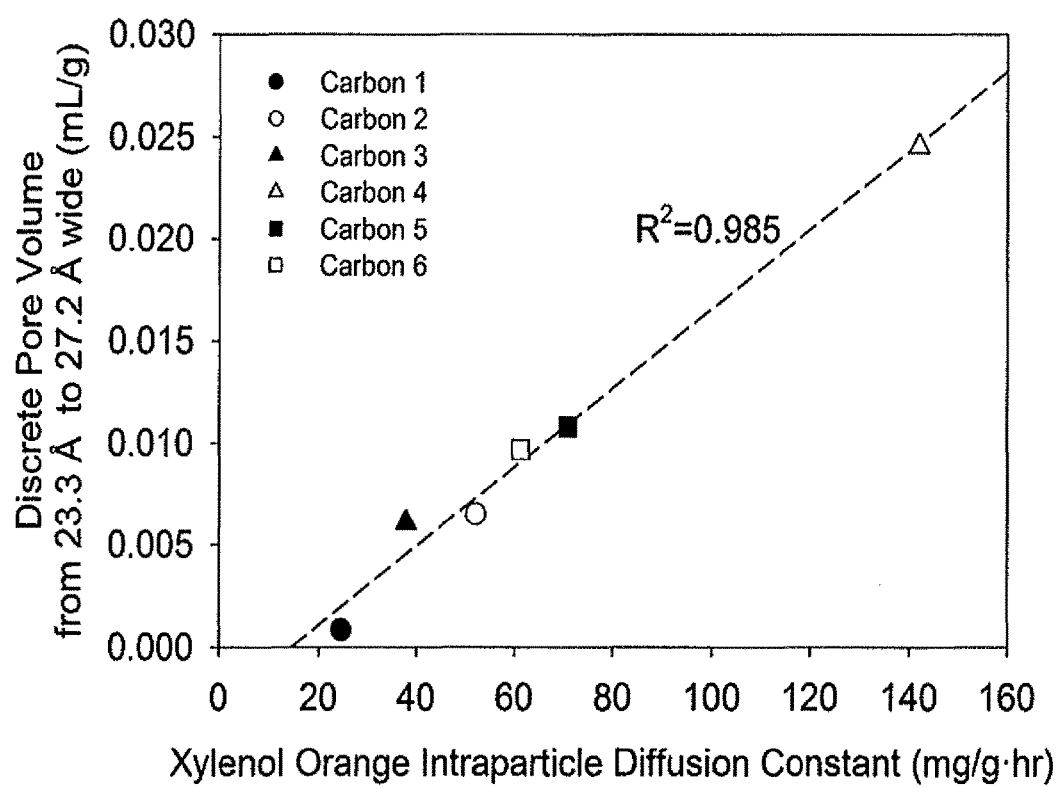

The intraparticle diffusion constant for each carbon type can then be correlated to the discrete pore volume for a given range of pore diameter. By this means the IDC can be used to determine important qualities regarding the mesopore structure of the carbon type, as shown in FIG. 15 which graphs the discrete pore volume from 23.3 Å to 27.2 Å versus the intraparticle diffusion constant (IDC) as determined from the adsorption of xylenol orange.

Table 1 shows the values displayed in FIG. 14, i.e., characteristics of coconut-shell based activated carbons as measured via: (a) Xylenol Orange adsorption and (b) Density Functional Theory as applied to argon gas adsorption isotherms.

|  | Intraparticle Diffusion Constant (mg/g/$hr^{1/2}$) | Volume (mL/g) of Pores 23.3 Å to 27.2 Å Wide |
|---|---|---|
| Carbon 1 | 24.6 | 0.0008 |
| Carbon 2 | 52.1 | 0.0065 |
| Carbon 3 | 37.9 | 0.0061 |
| Carbon 4 | 141.9 | 0.0245 |

-continued

|  | Intraparticle Diffusion Constant (mg/g/hr$^{1/2}$) | Volume (mL/g) of Pores 23.3 Å to 27.2 Å Wide |
|---|---|---|
| Carbon 5 | 70.8 | 0.0108 |
| Carbon 6 | 61.3 | 0.0097 |

Figure 16:
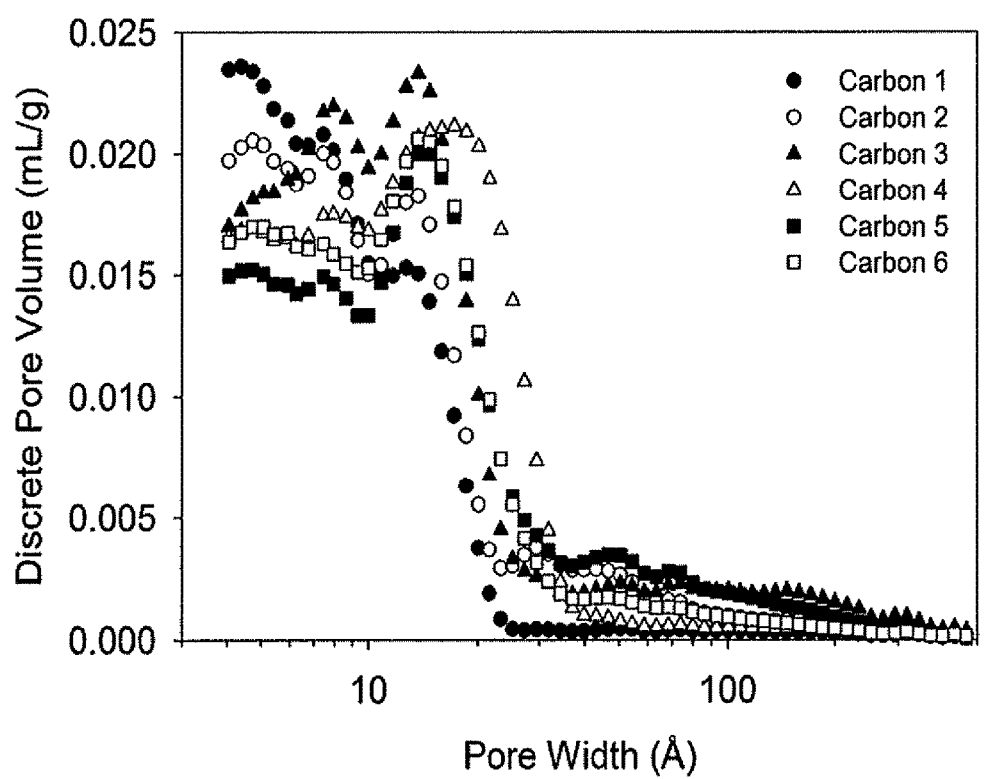

FIG. 16 shows discrete pore volume distributions for six coconut shell-based granular activated carbons from a range of 4.06 Å to 504 Å shown on a logarithmic scale. 4.06 Å is the smallest measurable pore size with argon adsorption isotherms and 504 Å is the probable limit of accuracy for this method.

Figure 17:
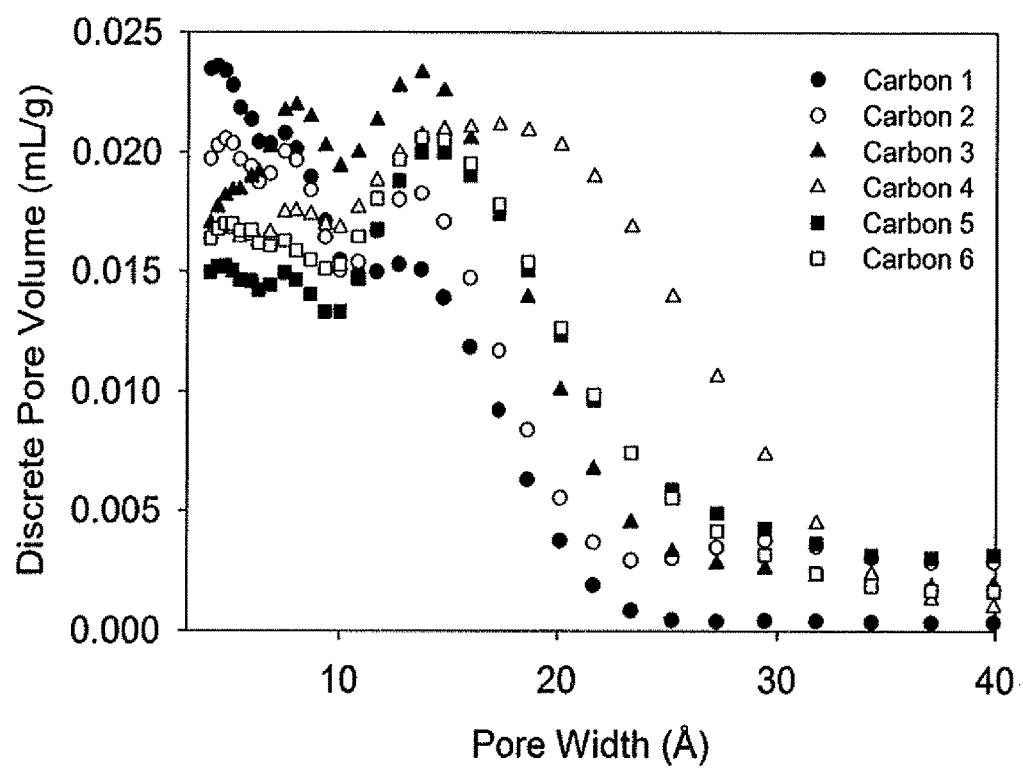

FIG. 17 shows the same data described in the above paragraph on a linear scale from a pore width of 4.06 Å to 40 Å.

EXAMPLE 11

Figure 18:
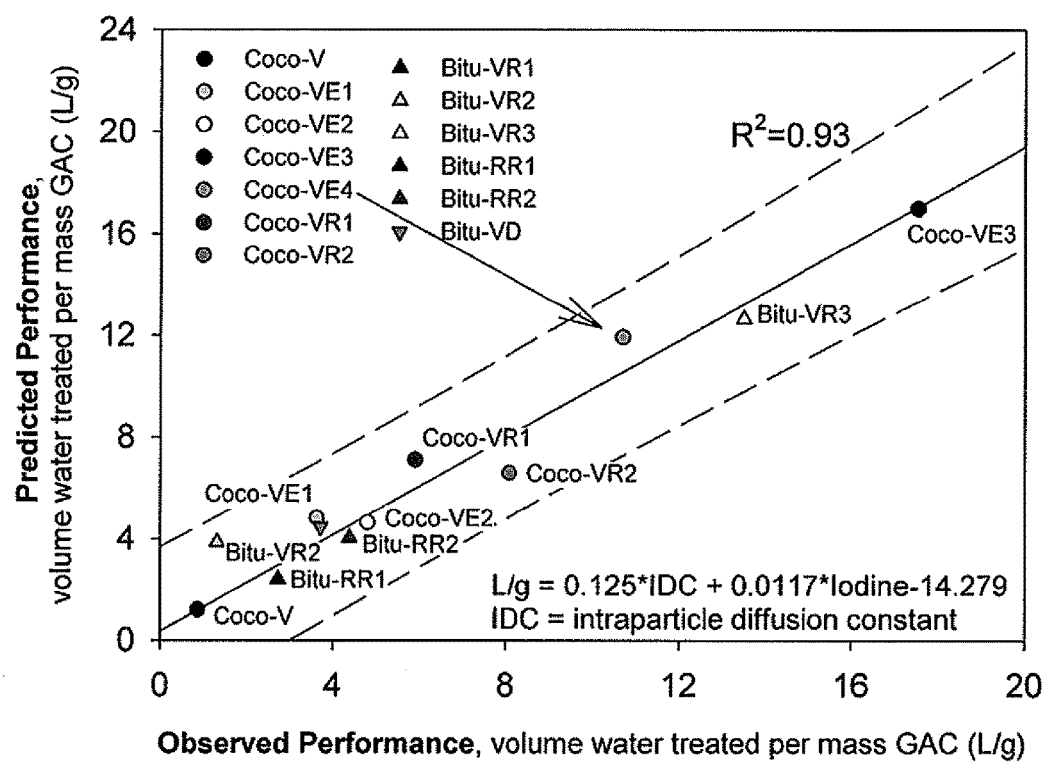

Various types of coconut based activated carbon were employed in removing 2-Methylisoborneol from river water. FIG. 18 shows the correlation between Observed Performance and Predicted Performance when using Intraparticle Diffusion Constant (IDC, mg/g/hr$^{0.5}$) and Iodine Number (mg/g) as predictors.

Figure 19:
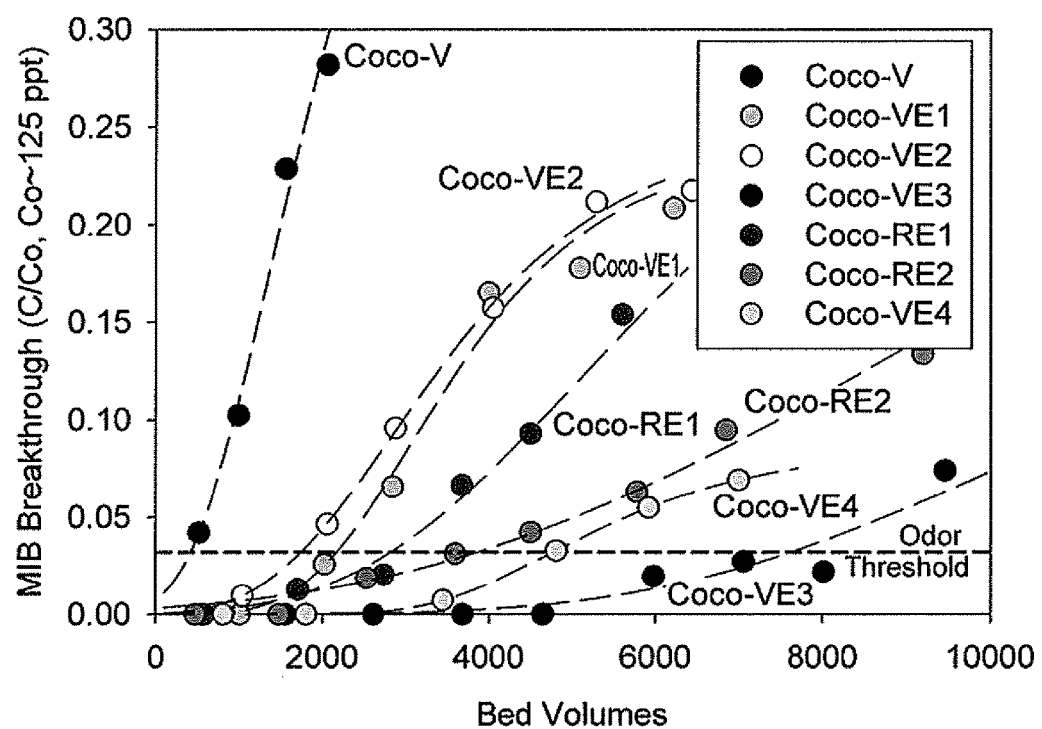

FIG. 19 shows the breakthrough of 2-methyisoborneol in RSSCTs. TOC~2.2 ppm. Coco-V has the earliest breakthrough and therefore poorest performance. Coco-VE3 has the latest breakthrough and therefore best performance.

Figure 20:
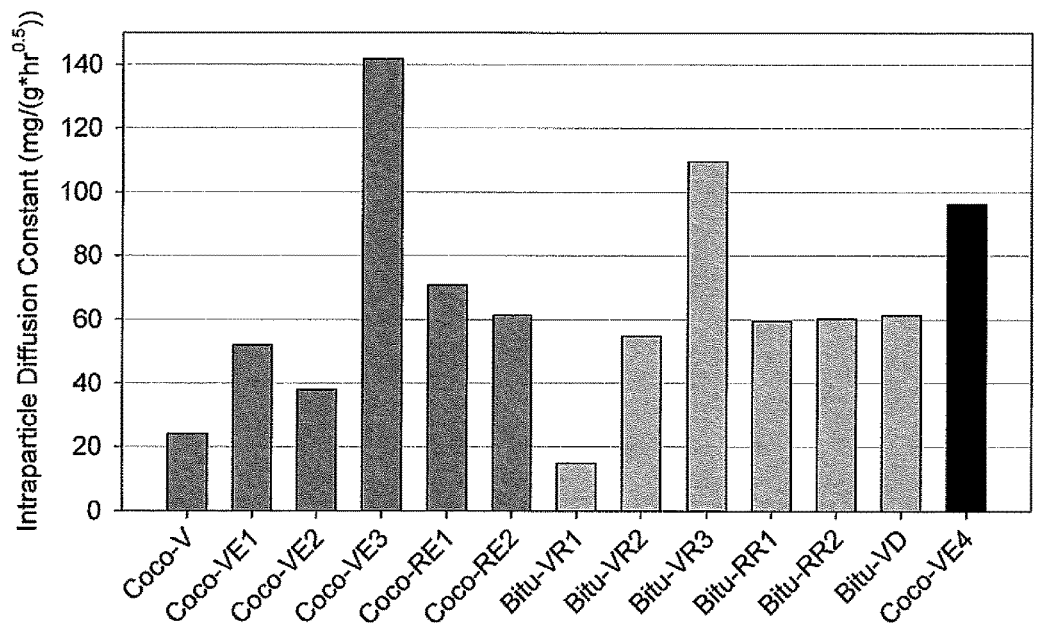

The IDC for each carbon type is shown in FIG. 20. Corresponding to the above figure, Coco-V has the lowest IDC while coco-VE3 has the highest IDC, demonstrating the relationship between performance and IDC.

Figure 21:
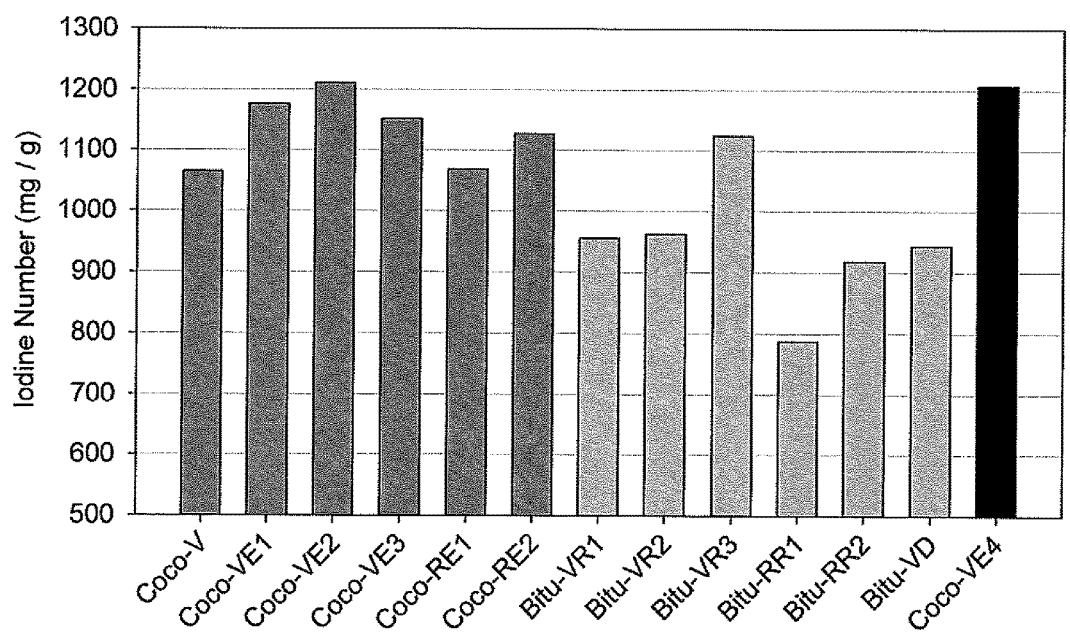

FIG. 21 shows the respective Iodine numbers from each carbon sample.

In accordance with one or more embodiments, the techniques disclosed herein may be applied to any type of carbon. In at least some embodiments, iodine number and dye number may be used in conjunction to characterize and predict carbon performance.

Having now described some illustrative embodiments, it should be apparent to those skilled in the art that the foregoing is merely illustrative and not limiting, having been presented by way of example only. Numerous modifications and other embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives.

It is to be appreciated that embodiments of the devices, systems and methods discussed herein are not limited in application to the details of construction and the arrangement of components set forth in the following description or illustrated in the accompanying drawings. The devices, systems and methods are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Those skilled in the art should appreciate that the parameters and configurations described herein are exemplary and that actual parameters and/or configurations will depend on the specific application in which the systems and techniques of the invention are used. Those skilled in the art should also recognize or be able to ascertain, using no more than routine experimentation, equivalents to the specific embodiments of the invention. It is therefore to be understood that the embodiments described herein are presented by way of example only and that, within the scope of the appended claims and equivalents thereto; the invention may be practiced otherwise than as specifically described.

Moreover, it should also be appreciated that the invention is directed to each feature, system, subsystem, or technique described herein and any combination of two or more features, systems, subsystems, or techniques described herein and any combination of two or more features, systems, subsystems, and/or methods, if such features, systems, subsystems, and techniques are not mutually inconsistent, is considered to be within the scope of the invention as embodied in the claims. Further, acts, elements, and features discussed only in connection with one embodiment are not intended to be excluded from a similar role in other embodiments.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of" are closed or semi-closed transitional phrases, respectively, with respect to the claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A method of producing an enhanced activated carbon, comprising:
   providing a predominantly microporous virgin activated carbon;
   introducing an aqueous calcium-based catalyst to the virgin activated carbon to produce a catalyst impregnated activated carbon;
   heating the catalyst impregnated activated carbon at a pyrolysis temperature until a mesopore volume of at least about 10% is achieved while substantially maintaining a micropore structure associated with the virgin activated carbon to produce the enhanced activated carbon;
   subjecting the enhanced activated carbon to a dye test to determine its intraparticle diffusion constant; and
   screening the enhanced activated carbon based on a threshold dye test number, wherein the threshold dye test number is at least about 40 mg/g/hr$^{1/2}$ for xylenol orange dye.

2. The method of claim 1, wherein the method is associated with a mass loss of at least about 10%.

3. The method of claim 1, wherein the aqueous calcium-based catalyst comprises calcium chloride.

4. The method of claim 1, wherein the aqueous calcium-based catalyst comprises a chelator.

5. The method of claim 4, wherein the chelator comprises citric acid.

6. The method of claim 1, wherein the virgin activated carbon is coconut shell-based.

7. The method of claim 1, wherein the virgin activated carbon is at least about 90% microporous.

8. The method of claim 1, wherein the catalyst impregnated activated carbon is maintained at an intermediate temperature prior to reaching the pyrolysis temperature.

9. The method of claim 1, wherein the virgin activated carbon is sprayed with or soaked in the aqueous calcium-based catalyst.

10. The method of claim 1, further comprising oxidizing the catalyst impregnated activated carbon with carbon dioxide.

11. The method of claim 10, wherein the catalyst impregnated activated carbon is oxidized with carbon dioxide and steam.

12. A method of producing an enhanced activated carbon, comprising:

providing a predominantly microporous virgin activated carbon;

introducing an aqueous calcium-based catalyst to the virgin activated carbon to produce a catalyst impregnated activated carbon;

heating the catalyst impregnated activated carbon at a pyrolysis temperature until a mesopore volume of at least about 10% is achieved while substantially maintaining a micropore structure associated with the virgin activated carbon to produce the enhanced activated carbon, wherein heating is performed until achieving an intraparticle diffusion constant of at least about 100 $mg/g/hr^{1/2}$;

subjecting the enhanced activated carbon to a dye test to determine its intraparticle diffusion constant; and screening the enhanced activated carbon based on a threshold dye test number.

* * * * *